United States Patent [19]

Uskokovic et al.

[11] 3,956,316

[45] May 11, 1976

[54] 11-SUBSTITUTED-DESA-PREGNANES AND DERIVATIVES THEREOF

[75] Inventors: Milan Radoje Uskokovic, Montclair; Thomas Henry Williams, Cedar Grove, both of N.J.

[73] Assignee: Hoffmann-La Roche Inc., Nutley, N.J.

[22] Filed: Dec. 26, 1973

[21] Appl. No.: 427,753

Related U.S. Application Data

[60] Continuation of Ser. No. 306,496, Nov. 14, 1972, Pat. No. 3,830,831, which is a continuation of Ser. No. 736,569, June 13, 1968, abandoned, which is a division of Ser. No. 499,094, Oct. 20, 1965, Pat. No. 3,574,761, which is a continuation-in-part of Ser. No. 400,206, Sept. 29, 1964, Pat. No. 3,412,107.

[52] U.S. Cl. .......................... 260/340.5; 260/340.7; 260/340.9; 260/345.8; 260/345.9; 260/455 R; 260/476 C; 260/488 B; 260/586 E
[51] Int. Cl.² .............. C07D 317/44; C07D 317/72; C07C 49/38; C07C 69/14

[58] Field of Search .......... 260/340.5, 340.9, 488 B, 260/586 E, 476 C, 455 R, 340.7, 389, 345.8, 345.9

[56] References Cited
UNITED STATES PATENTS

| 3,138,591 | 6/1964 | Nomine et al. .................. 260/586 E |
| 3,155,660 | 11/1964 | Nomine et al. .................. 260/586 E |
| 3,296,283 | 1/1967 | Cross ............................. 260/586 E |

*Primary Examiner*—Lorraine A. Weinberger
*Assistant Examiner*—Michael Shippen
*Attorney, Agent, or Firm*—Samuel L. Welt; Bernard S. Leon; Richard A. Gaither

[57] ABSTRACT

This invention is directed to 11-substituted-desA-pregnanes and derivatives thereof which are useful as intermediates in the production of 9$\beta$,10$\alpha$-known steroids of the pregnane series. These latter compounds can be utilized as progestational and salt-retaining agents.

5 Claims, No Drawings

11-SUBSTITUTED-DESA-PREGNANES AND DERIVATIVES THEREOF

RELATED APPLICATIONS

This application is a continuation of application Ser. No. 306,496, filed November 14, 1972, now U.S. Pat. No. 3,380,831, entitled "11-SUBSTITUTED-DESA-PREGNANES AND DERIVATIVES THEREOF", which is a continuation of application Ser. No. 736,569, filed June 13, 1968, now abandoned, entitled "11-SUBSTITUTED-DESA-PREGNANES AND DERIVATIVES THEREOF", which is a division of application Ser. No. 499,094, filed Oct. 20, 1965, now U.S. Pat. No. 3,574,761, entitled "INTERMEDIATES AND PROCESSES", which is a continuation-in-part of application Ser. No. 400,206, filed Sept. 29, 1964, now U.S. Pat. No. 3,412,107, entitled "INTERMEDIATES AND PROCESSES".

DETAILED DESCRIPTION OF THE INVENTION

This invention relates to novel chemical intermediates and processes useful in the preparation of steroids. Natural steroids possess a $9\alpha,10\beta$-stereochemical configuration. Steroidal compounds possessing the unnatural $9\beta,10\alpha$-configuration represent a pharmaceutically valuable class of compounds which, even though numerous members are known in the art, cannot be obtained by totally classical chemical means. In fact, the only known methods for obtaining steroids possessing the unnatural $9\beta,10\alpha$-configuration involve at least one photochemical reaction. Such photochemical reactions involve irradiation with ultraviolet light of strong intensity for long periods of time and, in comparison with purely chemical reactions, are very inefficient and give only small yields.

It is an object of the present invention to provide intermediates and processes which enable the preparation of $9\beta,10\alpha$-steroids without the necessity of proceeding through a photochemical reaction. It is also an object of this invention to provide novel intermediates and processes which will enable the further exploration of steroids having the unnatural $9\beta,10\alpha$-configuration.

It is also an object of this invention to provide novel $9\beta,10\alpha$-steroids.

The novel intermediates and processes of this invention are valuable and provide a new synthetic route completely of a classical chemical nature, i.e. involving no photochemical reaction, for converting steroids having the normal configuration into steroidal compounds possessing the unnatural $9\beta,10\alpha$-configuration.

In one aspect, the novel intermediates and processes of this invention enable the preparation of $9\beta,10\alpha$-steroids of the androstane series of the formula wherein $R_1$ is, individually, selected from the group consisting of hydroxy and lower alkanoyloxy; $R_2$ is, individually, hydrogen or lower alkyl and $R_1$ and $R_2$, taken together, are selected from the group consisting of ($17\beta$-OH, $17\alpha$-lower alkanoic acid lactone) and oxo; $R_3$ is selected from the group consisting of hydrogen, lower alkyl, hydroxy and lower alkanoyloxy; Y is selected from the group consisting of hydrogen and lower alkyl and X is a substituent in the 6- or 7-position selected from the group consisting of hydrogen, lower alkyl, lower alkylthio, lower alkanoylthio and halogen.

Compounds of formula I are useful as anabolic agents.

Other $9\beta,10\alpha$-androstanes, the preparation of which is enabled by the intermediates and processes of this invention, are of the formulae

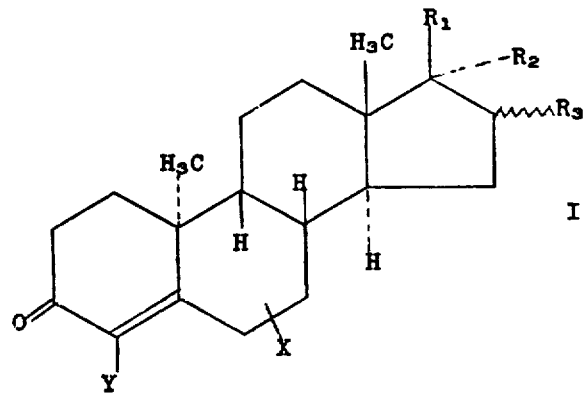

I

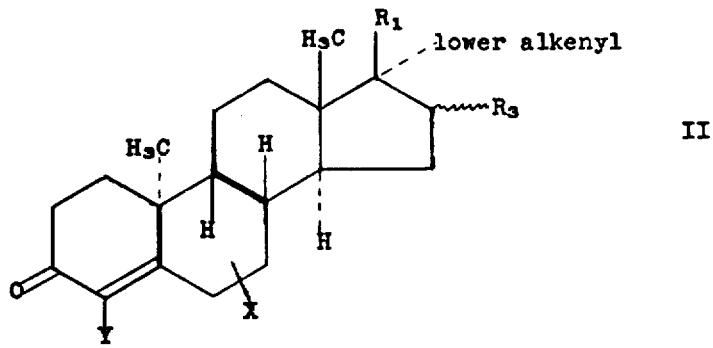

II

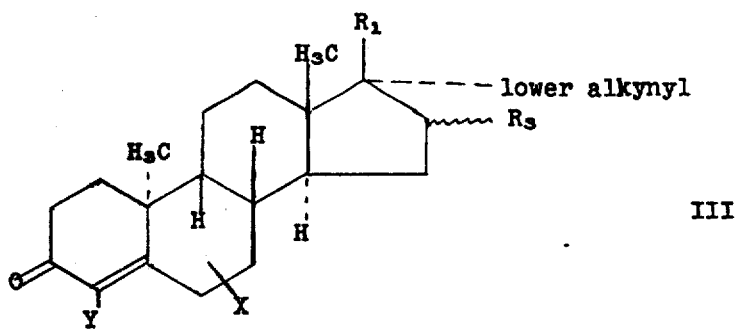

III wherein $R_1$, $R_3$, Y and X have the same meaning as above. Compounds of formula III are useful as progestational agents and compounds of formula II are useful as anti-androgenic agents.

In another embodiment of this invention, the novel compounds and intermediates provided by this invention enable the preparation of 9β,10α-steroids of the 17β-pregnane series of the formula

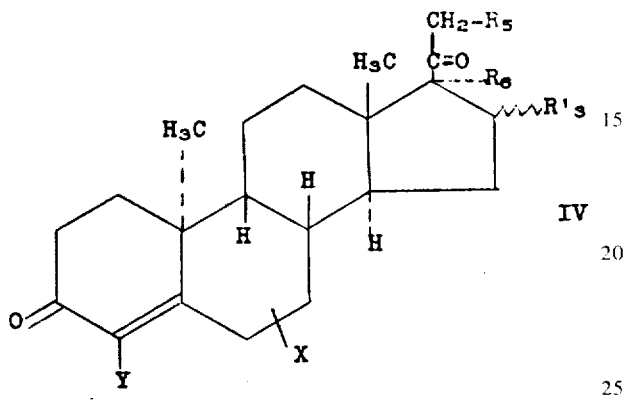

IV wherein Y and X have the same meaning as above; $R'_3$ is selected from the group consisting of hydrogen, lower alkyl, fluoro, hydroxy and lower alkanoyloxy; $R_5$ is selected from the group consisting of hydrogen and halogen; and $R_6$ is selected from the group consisting of hydrogen, lower alkyl, hydroxy and halogen.

Compounds of formula IV are useful as progestational agents.

Other 9β,10α-steroids of the 17β-pregnane series, preparable from the novel compounds and process of this invention, are of the formula

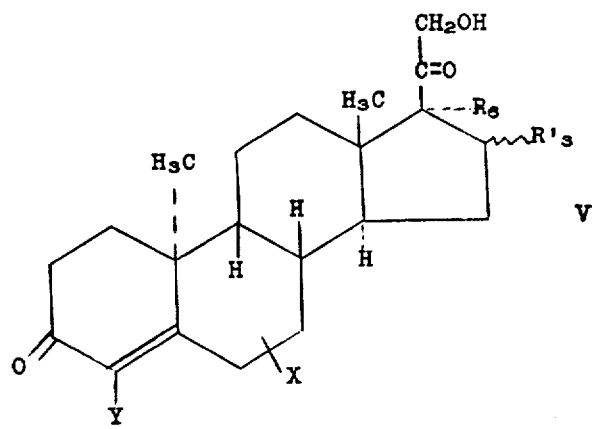

V wherein $R'_3$, $R_6$, Y and X have the same meaning as above.

Compounds of formula V are useful as salt-retaining agents, i.e. are useful in the treatment of Addison's disease.

As used herein, the term lower alkyl comprehends both straight and branched chain saturated hydrocarbon groups, such as methyl, ethyl, propyl, isopropyl and the like. Similarly, the term lower alkanoyl comprehends groups such as acetyl and the like, and the term lower alkanoyloxy comprehends groups e.g. formyloxyacetoxy and the like. In the same manner, the term lower alkenyl comprehends groups such as vinyl and the like, and the term lower alkynyl comprehends groups such as ethinyl and the like. Halogen comprehends all four halogens, i.e. iodine, bromine, chlorine and fluorine.

The expression "(17β-OH, 17α-lower alkanoic acid lactone)" refers to a configuration on the C-17 carbon atom illustrated as follows:

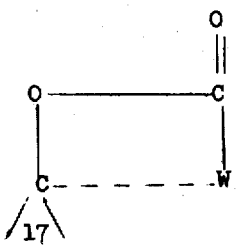

wherein W is lower alkylene, e.g. polymethylenes such as ethylene, propylene or the like.

With respect to substituents in the 6- and 7-position, preferred compounds are those having hydrogen or lower alkyl in 6- or 7-position, and those having halogen in the 7-position.

In one aspect, this invention comprises a method for the preparation of 9β,10α-androstanes of formulae I–III and of 9β,10α-17β-pregnanes of formulae IV–V which comprises the hydrogenation of desA-androst-9-en-5-ones or of desA-17β-pregn-9-en-5-ones to 9β,10β-desA-androstan-5-ones or 9β,10β-desA-17β-pregnan-5-ones, respectively, followed by condensation with a lower alkyl vinyl ketone with methyl or ethyl vinyl ketone preferred (as well as substitutes therefor such as 1-tertiary amino-3-butanone, 1-tertiary amino-3-pentanone and quaternary ammonium salts thereof), 1-Q-butan-3-one, 1-Q-butan-3-one lower alkylene ketal, 1-Q-butan-3-ol, esterified 1-Q-butan-3-ol, 1-Q-butan-3-ol ether, 1,3dichlorobut-2-ene, 1,3-dichloropent-2-ene, 1-pentan-3-one, 1-Q-pentan-3-one lower alkylene ketal, 1-Q-pentan-3-ol, esterified 1-Q-pentan-3-ol or 1-Q-pentan-3-ol ether, which condensation yields the desired 9β,10α-steroids. The symbol Q is is bromine, chlorine or iodine, with the former two being preferred. This invention also provides a number of different methods for the preparation of said desA-androst-9-en-5-one or desA-17β-pregn-9-en-5-one starting materials from natural steroids.

In one embodiment, a steroid of the 3-oxo-androst-4-ene or 3-oxo-17β-pregn-4-ene series is subjected to an oxidative ring opening of the A-ring yielding a 5-oxo-3,5-seco-A-norandrostan-3-oic acid or a 5-oxo-3,5-seco-A-nor-17β-pregnan-3-oic acid, which 3-oic acid can then be converted to a mixture of a 10α-desA-androstan-5-one and a 10β-desA-androstan-5-one or a mixture of a 10α-desA-17β-pregnan-5-one and a 10β-desA-17β-pregnan-5-one. The conversion of the 3-oic acid to the desA-compound can be effected either by pyrolysis of a salt of said 3-oic acid or via the enol lactone, i.e. a 4-oxoandrost-5-en-3-one or a 4-oxo-17β-pregn-5-en-3-one, which upon reaction with a Grignard reagent gives an aldol, which in turn can be converted into the desired desA-compound. The desA-compound can then be converted into the starting material desA-androst-9-en-5-one or desA-17β-pregn-9-en-5-one via a two-step sequence of halogenation and dehydrohalogenation.

In another embodiment of this invention, desA-androst-9-en-5-one or desA-17β-pregn-9-en-5-one starting materials can be prepared from 11-hydroxy steroids of the 3-oxo-androst-4-ene or 3-oxo-17β-pregn-4-ene series. This can be effected in a variety of ways. In one approach, an 11-hydroxy group of a steroid of the 3-oxo-androst-4-ene or 3-oxo-17β-pregn-4-ene series is converted into a leaving group, for example, a sulfonic acid ester or carboxylic acid ester. Oxidative ring opening of the A-ring of the thus formed 11-(esterified hydroxy)-containing compound yields the corresponding 11-(esterified hydroxy)-5-oxo-3,5-seco-A-norandrostan-3-oic acid or 11-(esterified hydroxy)-5-oxo-3,5-seco-A-nor-17β-pregnan-3-oic acid which upon pyrolysis of a salt of said 3-oic acid yields the desired desA-androst-9-en-5-one or desA-17β-pregn-9-en-5-one starting material.

A further approach involves formation of an 11-hydroxy-desA-androstan-5-one or 11-hydroxy-desA-17β-pregnan-5-one from an 11-hydroxy steroid of the 3-oxo-androst-4-ene or 3-oxo-17β-pregn-4-ene series via an oxidative ring opening of the A-ring of said 11-hydroxy steroid which yields an 11-hydroxy-5-oxo-A-nor-3,5-secoandrostan-3-oic acid 3,11-lactone or an 11-hydroxy-5-oxo-3,5-seco-17β-pregnan-3-oic acid 3,11-lactone which, in turn is converted into a salt of the corresponding keto acid which salt upon pyrolysis gives the 11-hydroxy-desA-androstan-5-one or 11-hydroxy-desA-17β-pregnan-5-one. Esterification of the 11-hydroxy moiety of the so-obtained compound with an acid moiety yields an 11-(esterified hydroxy)-desA-androstan-5-one or an 11-(esterified hydroxy)-desA-17β-pregnan-5-one which upon elimination of the leaving group (i.e., the esterified hydroxy moiety) gives the desired desA-androst-9-en-5-one or desA-17β-pregn-9-en-5-one starting material. Though, in the above reaction sequence either 11α-OH or 11β-OH starting material steroids can be used, it is preferred to use 11α-OH starting materials.

As will be appreciated from the above discussion, neither the specific reaction steps nor the reaction sequences of this invention involve any modification of substituents found in the 16- and/or 17-position of the starting material natural steroids. However, in order to obtain unnatural 9β,10α-steroids of formulae I-V, it is necessary or desirable to protect certain of the 16- and/or 17-substituents against one or more of the reaction steps involved. It is also convenient to initially protect such a substituent in the starting material natural steroid and maintain the substituent in its protected form throughout the entire reaction sequence, regenerating the desired substituent only when the steroid of formulae I-V possessing the unnatural 9β,10α-configuration is obtained. On the other hand, it is sometimes convenient to insert a protecting group only before a certain reaction step or sequence of reaction steps. Said protecting group can then be maintained until the final reaction step or can be split off at some intermediate stage. The protecting groups can be inserted and split off by means know per se. The desirability of having protecting groups present will be further discussed below when the specific reaction steps are discussed in detail. The various substituents which are susceptible to being protected are exemplified by the 16-hydroxy group in a compound of any of formulas I-V, the 17β-hydroxy group in a compound of any of formulas I-III, the 17α-hydroxy or 20-oxo group in a compound of any of formulas IV-V, the 21-hydroxy group of a compound of formula V or the 17-oxo group of a compound of formula I.

The 17-oxo or 20-oxo group is suitably protected by ketalization, i.e., by reaction with a lower alkanediol, to yield a 17-lower alkylene dioxy or 20-lower alkylene dioxy compound, i.e., a 17-ketal or a 20-ketal.

The 16-hydroxy, 17α-hydroxy, 17β-hydroxy or 21-hydroxy moieties can be protected by esterification and/or etherification of the hydroxy group. Any available acid which will form an ester that can subsequently be hydrolyzed to regenerate the hydroxy group is suitable. Exemplary acids useful for this purpose are lower alkanoic acids, e.g. acetic acid, caproic acid, benzoic acid, phosphoric acid and lower alkane dicarboxylic acids, e.g. succinic acid. Also, protection for the 16α-hydroxy, 17α-hydroxy, or 21-hydroxy substituent can be effected by forming the lower alkyl ortho ester thereof, i.e. 16α,17α- or 17α, 21-lower alkyl ortho esters. A suitable ether protecting group is, for example, the tetrahydropyranyl ether. Others are arylmethyl ethers such as, for example, the benzyl, benzhydryl and trityl ethers, or α-lower alkoxy-lower alkyl ethers, for example, the methoxymethyl, or allylic ethers.

In compounds containing the dihydroxyacetone side chain at C-17 (for example, compounds of formula V wherein $R_6$ is hydroxy), the side chain at C-17 can be protected by forming the 17,20; 20,21-bis-methylenedioxy group or by forming a 17,21-acetal or ketal group, or by forming a 17,21-diester. The 17,21-acetal or ketal and 17,21-diester hinder the 20-ketone group and minimize the possibility of its participating in unwanted side reactions. On the other hand, the 17,20;20,21-bis-methylenedioxy derivatives actually convert the ketone to a non-reactive derivative. When both a 16α-hydroxy and 17α-hydroxy substituent are present, these groups can be protected via formation of a 16α,17α-acetal or ketal. The various protecting groups mentioned above can be removed by means known per se, for example, by mild acid hydrolysis.

In compounds wherein there is present neither a 17α-hydroxy nor 21-hydroxy substituent but there is present a 20-oxo group, the 20-oxo group can be protected via reduction to the corresponding carbinol (hydroxy) group. Thus, for example, the 17-acetyl side chain can be protected via conversion to a 17-(α-hydroxyethyl)-side chain. Regeneration of the 17-acetyl side chain can be simply effected via conventional oxidation means, for example, via oxidation with chromium trioxide in an organic solvent such as glacial acetic acid. Similarly in compounds containing a 17-oxo, this group can be protected by reduction to the corresponding carbinol (hydroxy) group. Thus, the 17-oxo group can be reduced to a 17β-OH, 17α-H moiety, from which, when desired, the 17-oxo moiety can be regenerated by oxidation, as described above. Furthermore, a 20-hydroxy or 17β-hydroxy group, can itself be protected by esterification, for example, with a lower alkanoic acid such as acetic acid, caproic acid, or the like; or by etherification with moieties such as tetrahydropyranyl, benzyl, benzhydryl, trityl, allyl, or the like.

The 16α-17α or 17α,21-acetals and ketals above discussed can be formed by reacting 16α,17α-bishydroxy or 17α,21-bis-hydroxy starting materials with an aldehyde or a ketone; preferably it is done by reacting a simple acetal or ketal (i.e. a lower alkylene glycol acetal or ketal of a suitable aldehyde or ketone) with the moieties sought to be protected.

Suitable aldehydes and ketones include lower alkanals of at least two carbon atoms, such as paraldehyde, propanal and hexanal; di(lower alkyl)ketones, such as acetone, diethylketone, dibutylketone, methylethylketone, and methylisobutylketone; cycloalkanones, such as cyclobutanone, cyclopentanone and cyclohexanone; cycloalkyl (lower alkanals), such as cyclopentylcarboxaldehyde and cyclohexylcarboxaldehyde; cycloalkyl lower alkyl ketones, such as cyclopentyl propyl ketone, cyclohexylmethyl ethyl ketone; dicycloalkyl ketones, such as dicyclopentyl ketone, dicyclohexyl ketone and cyclopentyl cyclohexyl ketone; cycloalkyl monocyclic aromatic ketones, such as cyclohexyl p-chlorophenyl ketone, cyclopentyl o-methoxyphenyl ketone, cyclopentyl, o,p-dihydroxy-phenyl ketone and cyclohexyl m-tolyl ketone; cycloalkyl-lower alkyl monocyclic aromatic ketones, such as cyclopentylmethyl phenyl ketone; cycloalkyl monocyclic aromatic-lower alkyl ketones, such as cyclopentyl benzyl ketone and cyclohexyl phenethyl ketone; cycloalkyl-lower alkyl monocyclic aromatic-lower alkyl ketones, such as cyclopentylmethyl benzyl ketone; halo-lower alkanals, such as chloral hydrate, trifluoroacetaldehyde hemiacetal, and heptafluorobutanal ethyl hemiacetal; halo-lower alkanones, such as 1,1,1-trifluoroacetone; monocyclic carbocyclic aromatic aldehydes, such as benzaldehyde, halobenzaldehydes (e.g. p-chlorobenzaldehyde and p-fluorobenzaldehyde), lower alkoxy-benzaldehyes (e.g. o-anisaldehyde), di(lower alkoxy)benzaldehydes (e.g. veratraldehyde), hydroxybenzaldehydes (e.g. salicylaldehyde), lower alkyl benzaldehydes (e.g. m-tolualdehyde and p-ethylbenzaldehyde), di(lower alkyl)-benzaldehydes (e.g. o-p-dimethylbenzaldehyde); monocyclic carboxylic aromatic lower alkanals, such as phenylacetaldehyde, α-phenylpropionaldehyde, β-phenylpropionaldehyde, 4-phenylbutyraldehyde, and aromatically-substituted halo, lower alkoxy, hydroxy and lower alkyl cyano derivatives thereof; monocyclic carbocyclic aromatic ketones, such as acetophenone, α,α,α-trifluoroacetophenone, propiophenone, butyrophenone, valerophenone, halophenyl lower alkyl ketones (e.g. p-chloroacetophenone and p-chloropropiophenone); (lower alkoxy) phenyl lower alkyl ketones (e.g. p-anisyl methyl ketone); di-(lower alkoxy) phenyl lower alkyl ketones; hydroxy-phenyl lower alkyl ketones; (lower alkyl)phenyl lower alkyl ketones (e.g. methyl p-tolyl ketone); di(lower alkyl) phenyl lower alkyl ketones (o,p-xylyl methyl ketone; benzophenone, and mono- or bis-substituted halo, lower alkoxy, hydroxy and lower alkyl derivatives thereof; monocyclic carbocyclic aromatic lower alkanones, such as 1-phenyl-3-butanone and 1-phenyl-4-pentanone, and aromatically substituted derivatives thereof. Especially suitable are those aldehydes or ketones which, with the 16α,17α- or 17α,21-bis-hydroxy grouping form an acetal or ketal group of the formula

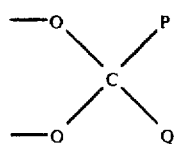

wherein P is individually selected from the group consisting of hydrogen and lower alkyl; Q is individually selected from the group consisting of lower alkyl and aryl; and P and Q taken together are lower alkylene.

The term "lower alkylene" comprehends polymethylene chains such as tetramethylene and pentamethylene.

In discussing the various starting materials, intermediates and end-products of this invention, the various protecting groups discussed above will not necessarily be specifically mentioned, but it should be understood that mention of any substituent comprehends the various protected forms thereof, unless specifically mentioned to the contrary.

In one embodiment of this invention, compounds of formula I through V are prepared from 9β,10β-desA-androstan-5-ones or 9β,10β-desA-pregnan-5-ones of the formula

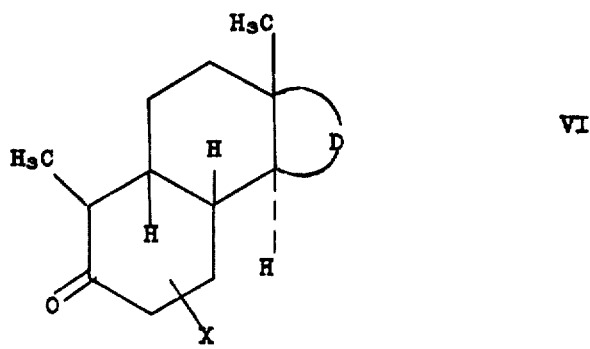

wherein X has the same meaning as above and D represents the carbon and hydrogen atoms necessary to complete the steroid D-ring, as well as the atoms in the substituents in the 16- and 17- positions, as defined in formulae I–V above.

Thus, 9β,10α-androstanes of formula I can be prepared from 9β,10β-desA-androstan-5-ones of the formula

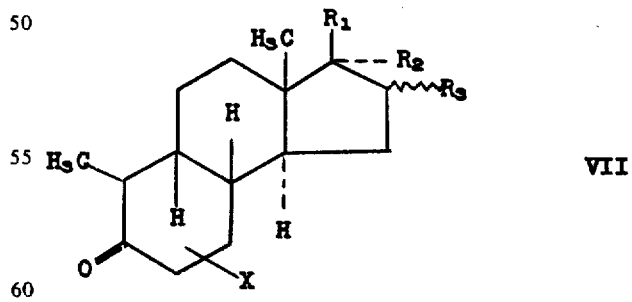

wherein $R_1$, $R_2$, $R_3$ and X have the same meaning as above.

Similarly, 9β,10α-androstanes of formula II can be prepared from 9β,10β-desA-androstan-5-ones of formula VIII and 9β,10α-androstanes of formula III from 9β,10β-desA-androstan-5-ones of formula IX.

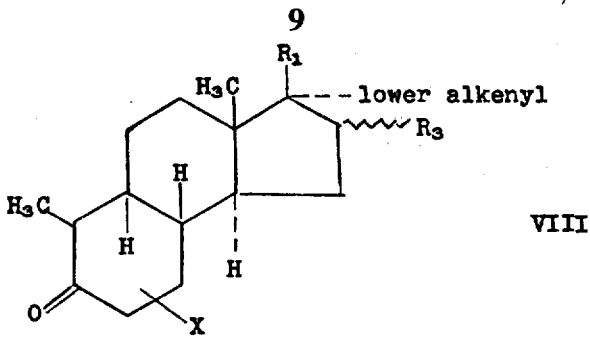

VIII

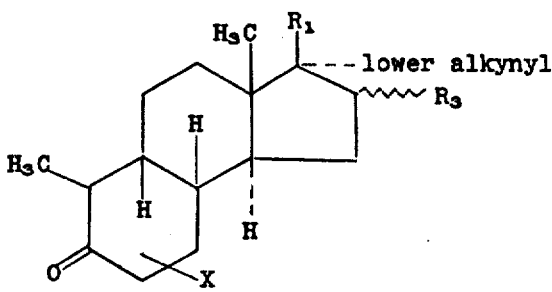

IX wherein R₁, R₃ and X have the same meaning as above.

Moreover, 9β,10α-17β-pregnanes of formulae IV and V can be prepared from 9β,10β-desA-pregnan-5-ones of formulae X and XI, respectively.

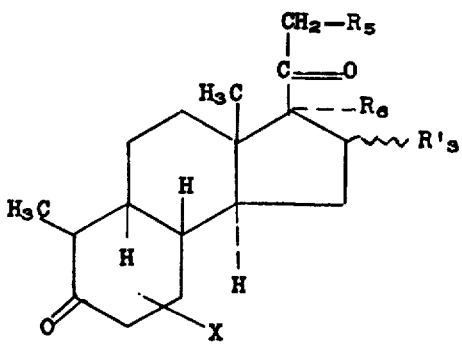

X

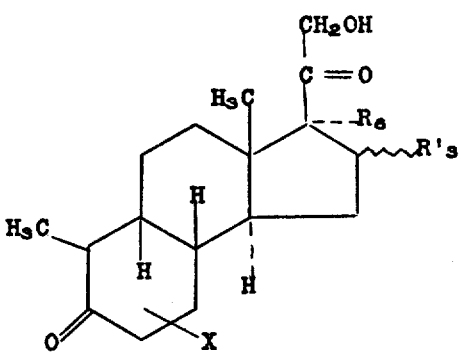

XI wherein R'₃, R₅, R₆ and X have the same meaning as above.

The conversion of a 9β,10β-desA-compound of formula VI to a 9β, 10α-steroid of formulae (i.e., VII → I, VIII → II, IX → III, X → IV and XI → V) is effected by condensing the 9β,10β-desA-compound with a compound selected from the group consisting of lower alkyl vinyl ketone (as well as substitutes therefor such as 1-tertiary amino-3-butanone, 1-tertiary amino-3-pentanone and quaternary ammonium salts thereof), 1,3-dichlorobut-2-ene, 1,3-dichloropent-2-ene, 1Q-butan-3-one, 1Q-butan-3-one lower alkylene ketal, 1Q-butan-3-ol, 1Q-butan-3-ol ether, esterified 1-Q-butan-3-ol, 1Q-pentan-3-one, 1Q-pentan-3-one lower alkylene ketal, 1Q-pentan-3-ol, 1-Q-pentan-3-ol ether or esterified 1-Q-pentan-3-ol. Q is bromo, chloro or iodo, with the former two being preferred. Methyl vinyl ketone and 1-tertiary amino-3-butanone are the preferred reagents, and the former is especially preferred. Prior to the condensation it is desirable to protect the 20-keto group present in compounds of formulae X and XI, then it is not necessary to protect 16α,17α or 21-hydroxy groups which are present, but groups protecting these moieties can be retained through the condensation reaction.

The above indicated substitutes for lower alkyl vinyl ketones are compounds wherein the vinyl moiety is replaced by a moiety of the formula

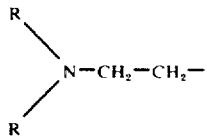

wherein each R is lower alkyl or taken together both R's are lower alkylene, oxa-lower alkylene or aza-lower alkylene. Such moieties are, for example, dimethylamino, diethylamino, pyrrolidino, piperidino, morpholino, or the like. The quaternary ammonium salts thereof are formed via the utilization of conventional quaternizing agents, for example, lower alkyl or phenyl-lower alkyl (especially benzyl) halides, mesylates or tosylates.

When a lower alkyl vinyl ketone or substitute therefor, 1-Q-butan-3-one or 1-Q-pentan-3-one is used as the reaction partner for the condensation, ring closure to ring A (containing a 3-oxo moiety) of the desired 9β,10α-steroid of formulae I-V occurs simultaneously with the condensation. However, when 1,3-dichlorobut-2-ene 1,3-dichloropent-2-ene, 1-Q-butan-3-one lower alkylene ketal, 1-Q-butan-3-ol, 1-Q-butan-3-ol ether, esterified 1-Q-butan-3-ol, 1-Q-pentan-3-one lower alkylene ketal, 1-Q-pentan-3-ol, 1-Q-pentan-3-ol ether, or esterified 1-Q-pentan-3-ol is used as the reaction partner a subsequent step to generate the 3-oxo moiety is required. When 1-Q-butan-3-ol or 1-Q-pentan-3-ol is used as the reaction partner, the oxo moiety can be generated by oxidation and for this purpose, it is suitable to use oxidation means known per se, for example, chromic acid, chromium trioxide in acetic acid or the like. When esterified or etherified 1-Q-butan-3-ol or esterified or etherified 1-Q-pentan-3-ol is used as the reaction partner, hydrolysis of the esterified or etherified hydroxy group should be effected prior to oxidation. Suitable ester forming moieties are, for example, carboxylic acids, e.g. lower alkanoic acid such as acetic acid, benzoic acid, and the like; and hydrolysis of the reaction products obtained by reacting such 1-Q-butan-3-ol or 1-Q-pentan-3-ol esters is suitably conducted by alkaline hydrolysis, e.g., via the use of an aqueous alkali metal hydroxide such as aqueous sodium hydroxide. Suitable ethers are, for example, lower alkyl ethers, i.e. 3-methoxy, 3-ethoxy or the like; and these are suitably hydrolyzed by acid hydrolysis, e.g. via the use of an aqueous mineral acid such as hydrochloric acid, sulfuric acid or the like. When a 1-Q-butan-3-one lower alkylene ketal or a 1-Q-pentan-3-one lower alkylene ketal is used as the reaction partner, mild acid hydrolysis of the ketal moiety results in generation of the 3-oxo moiety. Finally, when 1,3-dichlorobut-3-ene or 1,3-dichloropent-3-ene is used as the reaction partner, the 3-oxo moiety can be generated by treatment with a concentrated mineral acid, preferably a strong acid such as hydrochloric acid or sulfuric acid. It should be noted, the 1,3-dichlorobut-2-ene and 1,3-dichloropent-2-ene may be used as reaction partners with compounds of formulae X and XI, but not with the 17α-lower alkyl, alkenyl or alkynyl compounds of formulae VIII–IX. As will be apparent, when a reaction partner based on butane (i.e. having a four carbon atom skeleton) is utilized a compound of formulae I–V wherein Y is hydrogen is obtained. Similarly, when a reaction partner based on pentane is utilized a compound of formulae I–V wherein Y is methyl is obtained.

In addition to the preparation of compounds of formulae I–V from compounds of formulae VI–XI by the use of the above mentioned reaction partners, it is also possible by the procedures of this invention to prepare compounds of formulae I–V which, in the A-ring, in addition to containing an unsaturation between the 4-and 5-positions also contain an unsaturation between the 1- and 2-positions. Such 1,4-diene products corresponding to the compounds of formulae I–V can be prepared from compounds of formulae VI–XI by condensation of the latter with a reaction partner selected from the group consisting of ethinyl methyl ketone and ethinyl ethyl ketone (as well as substitutes therefor such as β-tertiary amino-vinyl methyl or ethyl ketone, quaternary ammonium salts thereof, and β-lower alkoxy-vinyl methyl or ethyl ketone). Condensation to prepare such a 1,4-diene product corresponding to the compounds of formulae I–V is effected under the same conditions as is the condensation to prepare a compound of formulae I–V. The so-obtained 1,4-dienes are useful in the same way as the correspondingly substituted 4-ene-compounds of formulae I–V.

The condensation is suitably effected at, below or above room temperature. For example, at the reflux temperature of the reaction medium or at ice temperature (0°C.) or below. Moreover, the condensation is suitably effected in an organic medium. Preferably the solvent is a lower alkanol, such as methanol, isopropanol, tert-butanol, ethanol, or another non-ketonic organic solvent, such as an ether, e.g. dioxane, diethyl ether, diisopropyl ether, aromatic hydrocarbon, e.g. benzene, toluene, xylene, organic acid, such as acetic acid, or the like. Lower alkanols are the preferred solvents. It is suitable to catalyze the condensation, and this can be effected via use of a catalyst such as an alkali metal lower alkoxide, for example sodium ethoxide, potassium t-butoxide, sodium t-amylate, or the like, alkali metal hydroxide such as sodium, lithium or potassium hydroxide, a quaternary ammonium hydroxide, for example, a benzyl tri-lower alkyl ammonium hydroxide such as benzyl trimethyl ammonium hydroxide, para-toluene sulfonic acid, or the like.

When using a substitute for methyl or ethyl vinyl ketone, or for methyl or ethyl ethinyl ketone, the condensation should be effected under alkaline conditions. As indicated above, among such substitutes are 1-tertiary amino-3-butanone, 1-tertiary amino-3-pentanone and β-tertiary amino-vinyl methyl or ethyl ketone. Preferred tertiary amino groups are dilower alkylamino groups such as dimethylamino, diethylamino, pyrrolidino, piperidino, morpholino, or the like. Preferred quaternary ammonium salts of such tertiary amino groups are, for example, those formed from lower alkyl halides such as methyl iodide. An exemplary β-lower alkoxy vinyl methyl or ethyl ketone is β-methoxyvinyl ethyl ketone.

One aspect of this invention is the hydrogenation of desA-androst-9-en-5-ones or desA-pregn-9-en-5-ones to 9β,10β-desA-androstan-5-ones of formulae VII–IX or to 9β,10β-desA-pregnan-5-ones of formulae X–XI. Thus, 9β,10β-desA-androstan-5-ones of formula VII can be prepared via hydrogenation of desA-androst-9-en-5-ones of the formulae

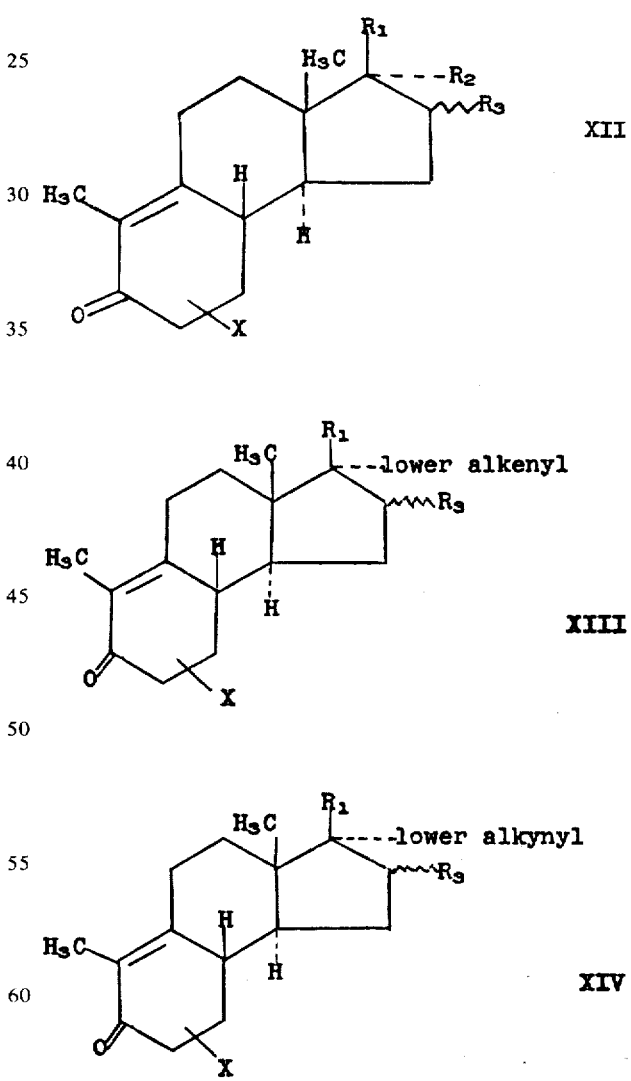

wherein $R_1$, $R_2$, $R_3$ and X have the same meaning as above.

Also, 9β,10β-desA-pregnan-5-ones of formulae X and XI can be prepared by hydrogenation of desA-pregn-9-en-5-ones of the formulae

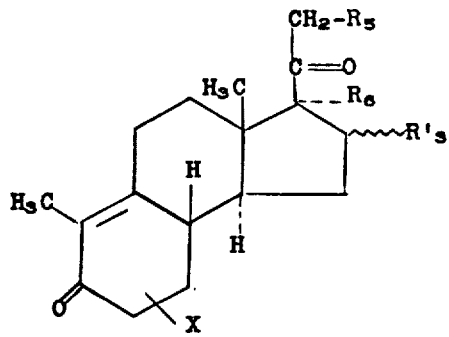

XV

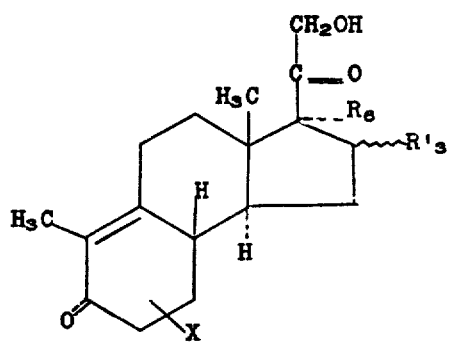

XVI wherein R'$_3$, R$_5$, R$_6$ and X have the same meaning as above.

Prior to hydrogenation, the C-20 keto group in compounds of formulae XV and XVI or C-17 keto group in compounds of formula XII should be protected either by conversion to the corresponding carbinol or by ketalization as described above. The hydrogenation can, however, be effected without protecting such keto groups.

Moreover, it should be noted that the hydrogenation, besides inserting a hydrogen atom in each of the 9- and 10-positions, can also simultaneously effect hydrogenation of other groups in the molecule. For example, the C-20-keto group can be hydrogenated to the corresponding carbinol or the C-17 lower alkenyl group in compounds of formula XIII or the C-17 lower alkynyl group in compounds of formula XIV can be hydrogenated to the corresponding C-17-lower alkyl compounds. Compounds of formulae VIII and IX can, in turn, be prepared from compounds of formula VII wherein R$_1$ and R$_2$ together are oxo via reaction with a lower alkenyl or lower alkynyl Grignard reagent, with prior protection of the 5-keto group, for example, by forming 5-ketals without concurrent blocking of the 17-keto group. In the same manner compounds of formulae XIII and XIV can be formed from compounds of formula XII wherein R$_1$ and R$_2$ taken together are oxo.

The hydrogenation of desA-androst-9-en-5-ones of formulae XII–XIV and of desA-pregn-9-en-5-ones of formulae XV–XVI is one of the main features of this invention. It is effected by catalytic hydrogenation, suitably using a precious metal catalyst. Suitable precious metal catalysts are palladium, platinum, ruthenium, and rhodium, the latter two being especially preferred. It is particularly advantageous to use rhodium, for example, rhodium on charcoal (or carbon powder, carbon black, or the like) or rhodium on alumina. In contrast to what would be expected, it has been found that such a catalytic hydrogenation of a compound of formulae XII–XVI gives a substantial yield of a compound of formulae VI–XI. In fact, it has been found that such catalytic hydrogenation gives a major proportion of a compound of the formulae VI–XI. This catalytic hydrogenation is suitably effected in an inert organic solvent, for example, a lower alkanol such as methanol or ethanol, an ether such as dioxane or diglyme, a hydrocarbon such as cyclohexane, hexane, or the like. Lower alkanols are preferred solvents. Moreover, it is suitably conducted in the presence of an acidic or basic catalyst, for example, an alkali metal or alkaline earth metal hydroxide such as sodium hydroxide or the like, or a mineral acid, for example, a hydrohalic acid, such as hydrochloric acid, or the like, or an organic acid such as a lower alkanoic acid, for example, acetic acid. The reaction can be conducted at, above or below room temperature, for example, from about −5°C. to about 100°C. However, it is preferably conducted at a temperature between about 0°C. and about 35°C.

As described above, the desA-androst-9-ene-5-ones or desA-17β-pregn-9-en-5-ones of formulae XII-XVI can be prepared from natural steroids by a variety of methods. Thus, in one embodiment of this invention said desA-androst -9-en-5-ones or desA-17β-pregn-9-en-5-ones can be prepared from steroids of the 3-oxo-androst-4-ene or 3-oxo-17β-pregn-4-ene series by a reaction sequence which involves as a first step an oxidative ring opening of ring A of the natural steroid. For this oxidative ring opening there can be used as starting materials, natural steroids of the 3-oxo-androst-4-ene or 3-oxo-17β-pregn-4-ene series of the formula:

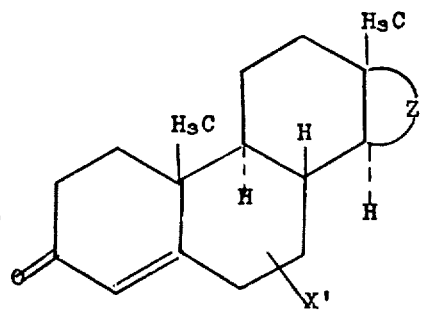

XVII wherein X' is a substituent in the 6-position selected from the group consisting of hydrogen, lower alkyl, lower alkylthio and lower alkanoylthio or a substituent in the 7-position selected from the group consisting of hydrogen, lower alkyl, lower alkylthio, lower alkanoylthio and halogen, and Z represents the carbon and hydrogen atoms necessary to complete the steroid D-ring, as well as the atoms in the substituents in the 16- and 17-positions as defined in formulae I, IV, and V above.

The oxidative ring opening of a natural steroid of formula XVII yields a 5-oxo-3,5-seco-A-norandrostan-3-oic acid or a 5-oxo-3,5-seco-A-norpregnan-3-oic acid of the formula

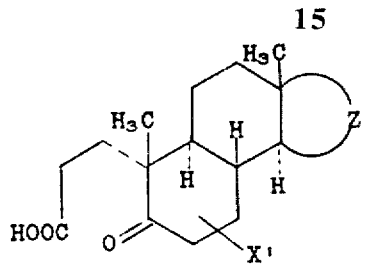

XVIII wherein X' and Z have the same meaning as above. The oxidative ring opening of the compound of formula XVII can be performed by a variety of methods. In a preferred embodiment it is effected by ozonolysis. The ozonolysis is suitably carried out in an organic solvent, for example, acetic acid, ethyl acetate, methanol, chloroform, methylene chloride, or the like, or a mixture of two or more of such solvents such as ethyl acetate/acetic acid, ethyl acetate/methylene chloride, or the like. Moreover, the ozonolysis is advantageously conducted at below room temperature. Thus, it is preferably conducted at a temperature between about −70°C. and about 25°C. The resulting ozonides can be decomposed by conventional means, for example, by treatment with water, hydrogen peroxide in water, acetic acid or ethyl acetate, or the like. The oxidative ring opening of a compound of formula XVII to a compound of formula XVIII can also be effected by other oxidation means, for example, by treatment with hydrogen peroxide. It should be noted that an oxidative ring opening by either ozonolysis or by treatment with hydrogen peroxide, does not require protection of any of the substituents at C-16 or C-17. However, as stated above, it may be desirable to protect these substituents against some subsequent reaction in the total reaction sequence being practiced. On the other hand, the oxidative ring opening can also be effected by oxidation with chromium trioxide or via treatment with sodium periodate and potassium permanganate in potassium carbonate solution and if these oxidation means are used, it is necessary to protect any secondary hydroxy groups which might be present such as a 16,17β- or 21-hydroxy group; preferably, for the purpose of this reaction, with non-aromatic protecting groups.

Following the oxidative ring opening of the A-ring, the so-obtained 5-oxo-3,5-seco-A-norandrostan-3-oic acid or 5-oxo-3,5-seco-A-norpregnan-3-oic acid of formula XVIII is converted into a mixture of a 10α-desA-androstan-5-one and a 10β-desA-androstan-5-one one or a mixture of a 10α-desA-pregnan-5-one and a 10β-desA-pregnan-5-one as illustrated below:

wherein in formulae XIX and XX, X' and Z have the same meaning as above.

The compounds of formula XIX are 10α-desA-androstan-5-ones or 10α-desA-pregnan-5ones, depending on the meaning of Z, and the compounds of formula XX are 10β-desA-androstan-5-ones or 10β-desA-pregnan-5-ones. The conversion of a compound of formula XVIII into the compounds of formula XIX and XX is effected by pyrolysis. In effecting the pyrolysis, it is desirable to convert the 3-oic acid of formula XVIII into a corresponding metal salt, for example, an alkali metal salt such as the sodium or lithium salt. This conversion to a metal salt can be effected prior to pyrolysis, e.g., by treating the acid sodium hydroxide or in situ during the course of the pyrolysis, e.g., by fusing the 3-oic acid with a mixture of sodium acetate and potassium acetate. The pyrolysis can be conducted at atmospheric pressure or in a vacuum. One preferable embodiment is to conduct the pyrolysis in a vacuum, at a temperature from about 200°C. to about 350°C. in the presence of a proton acceptor, e.g. an alkali metal or alkaline earth metal salt of a weak organic acid, for example, potassium acetate, sodium acetate, sodium phenyl-acetate, sodium bicarbonate, or the like; especially preferred is a vacuum of from about 0.001 to about 0.5 mm. Hg. Accordingly, it is advantageous to conduct the pyrolysis under alkaline conditions, i.e. at a pH greater than 7. The pyrolysis can be effected in solution or by fusion. An especially preferred method of effecting the pyrolysis is by fusion of an alkali metal salt of a weak acid, for example, an organic carboxylic acid such as a lower alkanoic acid or a phenyl-lower alkanoic acid such as phenyl-acetic acid. Another method of effecting the pyrolysis is to heat, preferably at atmospheric pressure, a solution of an alkali metal salt, such as the sodium or lithium salt, of a 3-oic acid of formula XVIII in a basic organic solvent. The basic organic solvent should, of course, be one which is in the liquid state at the temperature at which the pyrolysis is effected. Thus, the pyrolysis can be effected at a temperature up to the boiling point of the basic organic solvent being used. Suitable basic organic solvents are, for example, nitrogen containing organic solvents such as piperidine, pyridine, isoquinoline, quinoline, triethanolamine, or the like. When utilizing this approach using a basic organic solvent it is suitable to heat to temperature between about 200°C. and about 300°C., and preferably between about 230°C. and about 260°C. A preferred basic organic solvent for the pyrolysis of a salt of a compound of formula XVIII to compounds of formulae XIX and XX is quinoline. If a basic organic solvent is used which boils substantially below 200°C. at atmospheric pressure, it is suitable to conduct the pyrolysis in a sealed tube or an autoclave.

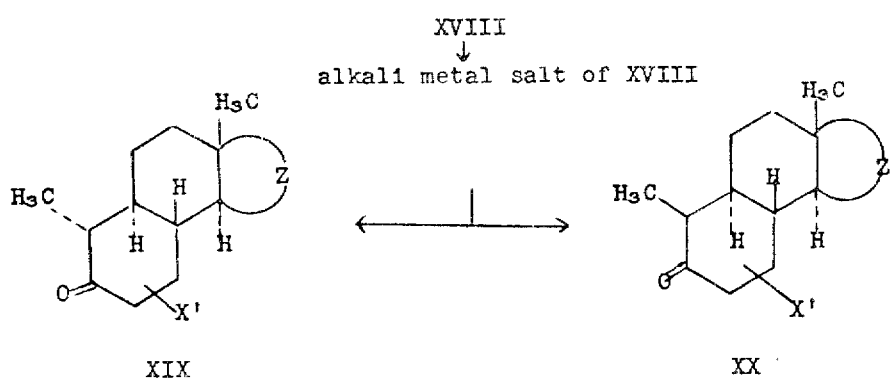

In another aspect, compounds of formula XIX can be prepared from compounds of the formula

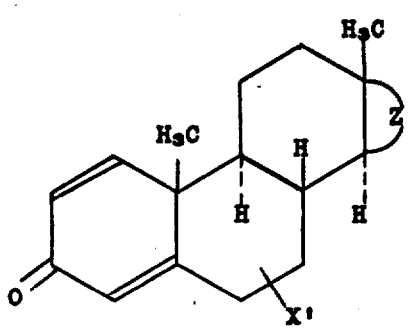

XIX A wherein X' and Z have the same meaning as above. The compounds of formula XIX can be prepared from compounds of formula XIX A in the same manner that compounds of formula XIX are prepared from compounds of formula XVII, i.e. by oxidative ring opening of the A-ring of a compound XIX A followed by elimination of the residue of the A-ring, to yield a compound of formula XIX. The oxidative ring opening of the compound of XIX A can be performed by ozonolysis as described above for the conversion of a compound of formula XVII to a compound of formula XVIII. Such ozonolysis of a compound of formula XIX A yields a compound of the formula

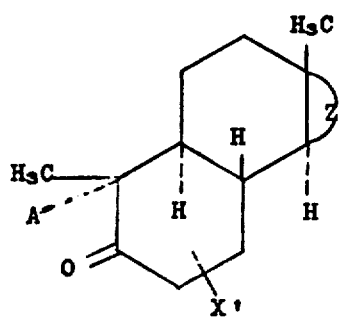

XIX B wherein X' and Z have the same meaning as above, and A is carboxy or formyl.

A compound of formula XIX B can then be converted to a compound of formula XIX. This removal of the residue of the A-ring, i.e. decarboxylation and deformylation, can be effected by heating in an acidic or basic medium. It is preferred to heat to the reflux temperature of the medium which is preferably an inert organic solvent such as a lower alkanol, e.g. ethanol, dioxane, ether or the like. The decarboxylation and deformylation yields mainly a compound of formula XIX, but also a minor yield of the corresponding 10β-isomer of formula XX.

Compounds of formula XIX can also be formed from a compound of formula XVIII via the formation of an enol-lactone of a compound of formula XVIII, i.e. via the formation of a 4-oxo-androst-5-en-3-one or a 4-oxo-pregn-5-en-3-one of the formula:

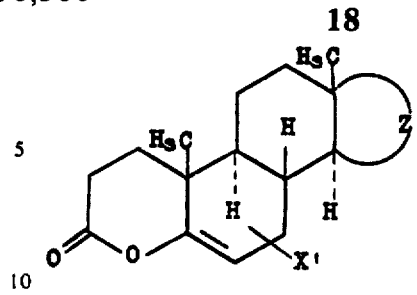

XXI wherein X' and Z have the same meaning as above, which can then be reacted with a Grignard reagent, such as phenyl magnesium bromide or phenyl lithium, to form the resulting aldol of, for example, the formula

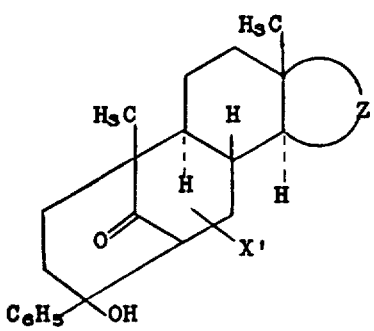

XXII wherein X' and Z have the same meaning as above, which, upon treatment with an alkali metal hydroxide, such as potassium hydorxide, at an elevated temperature, for example, from about 200°C. to about 240°C., is converted to the corresponding 10α-desA-androstan-5-one or 10α-desA-pregnan-5-one of formula XIX.

It should be noted that though the pyrolysis of a compound of formula XVIII yields both the 10β-compounds of formula XX and the 10α-compounds of formula XIX, and though either of these isomers can be used in the subsequent halogenation and dehydrohalogenation steps of this reaction sequence, it is sometimes preferable to convert the 10β-compound of formula XX into the corresponding 10α-compound of formula XIX. This conversion can be effected by treating a 10β-desA-androstan-5-one or 10β-desA-pregnan-5-one of formula XX with any base capable of producing a carbanion; for example, it is suitable to use an alkali metal lower alkoxide in an organic solvent such as a lower alkanol, for example, sodium ethoxide in an ethanol solution or sodium methoxide in a methanol solution.

The above-discussed conversion via the alkali metal salt and pyrolysis of compounds of formula XVIII to compounds of formulas XIX and XX can be effected without protection of any of the substituents which might be present at C-16 or C-17. However, if it is desired for either preceding or succeeding reaction steps of the total reaction sequence, the conversion of a compound of formula XVIII to compounds of formulas XIX and XX can be effected with protecting groups present on substituents in the C-16 or C-17 position.

As stated above, the 10α-desA-androstan-5-ones or 10α-desA-pregnan-5-ones of formula XIX or the 10β-desA-androstan-5-ones of 10β-desA-pregnan-5-ones of formula XX can be converted via a two-step sequence of halogenation and dehydrohalogenation into the desired starting material desA-androst-9-en-5-one or desA-pregn-9-en-5-one of formulas XII, XV, and XVI.

In a preferred embodiment a 10α-desA-androstan-5-one or a 10α-desA-pregnan-5-one of formula XIX is subjected to the two-step sequence of halogenation and dehydrohalogenation. Halogenation of a compound of formula XIX or a compound of formula XX yields a mixture of corresponding halogenated compounds including one of the formula

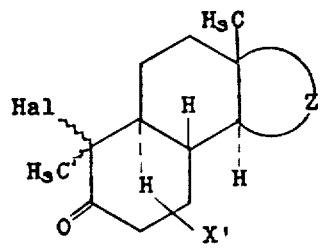

XXIII wherein X' and Z have the same meaning as above, and Hal is a halogen atom (preferably Br or Cl). Dehydrohalogenation of a compound of formula XXIII then yields a desired starting material of formulas XII, XV and XVI. Keto groups except for the 5-keto group, may require protection prior to the halogenation. In the case of compounds of formulas XIX and XX containing the C-17 dihydroxyacetone side chain, represented in formula V wherein $R_6$ is hydroxy, this protection can be effected by formation of the 17α,20;20,21-bis-methylenedioxy derivative. In other cases wherein a C-17 oxo or C-20 oxo group is present, protection can be effected by reduction to the corresponding carbinol directly prior to the halogenation step or prior to some other step in the reaction sequence leading to the compounds of formulas XIX and XX.

The halogenation can be effected with halogenating agents such as bromine, sulfuryl chloride, or the like. Bromination is especially preferred. The bromination is suitably effected by treatment with bromine at room temperature or below, preferably at ice temperature or below. Suitably it is conducted in an organic medium; for example, an organic acid such as acetic acid; an ether such as an anhydrous ether, dioxane, tetrahydrofuran; a chlorinated organic solvent such as methylene chloride, chloroform, carbon tetrachloride; or the like; with the addition of hydrogen bromide as a catalyst. When effecting halogenation with sulfuryl chloride, it is suitable to use the same type of organic medium as when brominating; and suitable catalysts are, for example, acetic acid, benzoyl peroxide, or the like.

The subsequent dehydrohalogenation of a compound of formula XXIII is preferably conducted under mild dehydrohalogenating conditions; for example, by the use of an alkali metal carbonate (e.g. lithium carbonate) or an alkali metal halogenide (e.g. a lithium halide) in an organic solvent such as a di-lower alkyl-formamide, or with an organic base such as collidine, pyridine, or the like. The dehydrohalogenation is advantageously conducted at slightly elevated temperatures, for example, from about 50°C. to about 150°C., preferably from about 80°C. to about 120°C.

Separation of the desired product desA-androst-9-en-5-one or desA-pregn-9-en-5-one of formulas XII, XV and XVI can be effected by conventional means. As indicated above the halogenation procedure may result in halogenated by-products in addition to the desired intermediate of formula XXIII. Accordingly, the separation is preferably effected after first subjecting the reaction mixture to dehalogenating conditions in order to dehalogenate the halogenated by-products formed by the halogenation procedure, but not dehalogenated by the dehydrohalogenation. Following such dehalogenation the reaction mixture can then easily be separated by conventional means, for example, by column chromatography, to yield the desired compound of formulas XII, XV, XVI. An examplary dehalogenation means is treatment with zinc and sodium acetate in an acetic acid solution at an elevated temperature, for example, about 80°C.

In the case of compounds of formulas XIX or XX which contain a halogen atom on a carbon atom directly adjacent to a keto group, it is preferable to protect such a halogen atom against dehalogenation prior to subjecting the compound of formulas XIX or XX to the two step sequence of halogenation and dehydrohalogenation of this embodiment. Such a grouping, containing a halogen atom on a carbon atom directly adjacent to a keto group, is illustrated in a compound of formulas IV or V wherein $R_5$ or $R_6$ is halogen. Thus, if 10α- or 10β-desA-pregnan-5-one of formulas XIX or XX containing a 17α- or 21-halo substituent is to be subjected to the halogenation-dehydrohalogenation sequence it is desirable to first effect protection of the 17α- or 21-halo substituent. This protection can be effected, for example, by ketalization of the 20-oxo group.

As stated above, the desired desA-androst-9-en-5-ones or desA-pregn-9-en-5-ones starting materials can also be prepared from steroids of the 3-oxo-androst-4-ene or 3-oxo-17β-pregn-4-ene series containing an 11-hydroxy substituent. In one embodiment an 11-hydroxy steroid of the formula

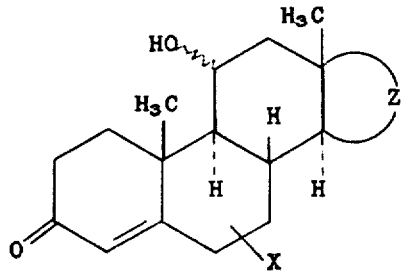

XXIV wherein X and Z have the same meaning as above, is reacted with an acid or a reactive derivative thereof to form a leaving group in the 11-position. By reactive derivative is meant, for example, a halide, e.g. a chloride, an anhydride, or the like. Though either 11β- or 11α-hydroxy starting materials can be used, it is preferable to utilize α-hydroxy compounds of formula XXIV as starting materials. Prior to the esterification reaction, it is preferable to protect hydroxy groups present in the C-16, C-17, or C-21 position. Suitable acids for the esterification of the 11-hydroxy group, which can be used to form a leaving group in the 11-position are inorganic acids such as phosphoric acid, organic carboxylic acids such as anthraquinone β-carboxylic acid or organic sulfonic acids, for example, toluene-sulfonic acids, especially p-toluene sulfonic acid, lower alkyl-sulfonic acids such as methane-sulfonic acid and nitrophenyl-sulfonic acids, especially p-nitrophenylsulfonic acid. Especially preferred as the leaving group in the 11-position is a lower alkylsulfonyloxy group such as the mesoxy group. However, when it is desired to react a compound of formula XXIV with a sulfonyloxy forming moiety, then a compound of formula XXIV having an 11α-configuration should be used as a starting material. The above described esterification of 11-hydroxy steroid starting materials of formula XXIV yields compounds of the formula

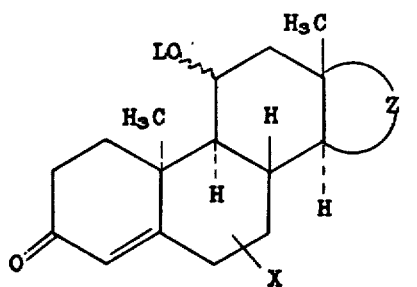

XXV wherein X and Z have the same meaning as above, and LO represents the leaving group.

In the next step of this reaction sequence, the so-formed 11-(esterified hydroxy)-compound of formula XXV is subjected to an oxidative ring opening of the A-ring to yield the corresponding 11-(esterified hydroxy)-5-oxo-3,5-seco-A-norandrostan-3-oic acid or 11-(esterified hydroxy)-5-oxo-3,5-seco-A-norpregnan-3-oic acid of the formula

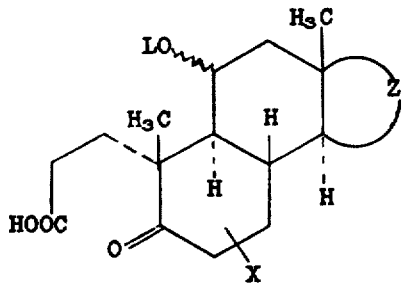

XXVI wherein X, Z and LO have the same meaning as above.

The oxidative ring opening of the A-ring of a compound of formula XXV to a compound of formula XXVI can be effected by ozonolysis as described above, for the oxidative ring opening of the A-ring of a compound of formula XVII to a compound of formula XVIII. Pyrolysis of the so-formed compound of formula XXVI under the conditions described above for the pyrolysis of a compound of formula XVIII to compounds of the formulas XIX and XX directly yields the desired desA-androst-9-en-5-one or desA-pregn-9-en-5-one of formulas XII, XV, XVI. Thus, pyrolysis of a compound of formula XXVI directly results in elimination of the leaving group in the 11-position as well as a splitting off of the residue of ring A attached to the 10-position. This procedure of starting from an 11-hydroxy steroid (preferably 11α-hydroxy) of formula XXIV and proceeding through intermediates of formulas XXV and XXVI to compounds of formulas XII, XV, XVI, represents a particularly elegant procedure for preparing the latter compounds. An especially preferred method of effecting the pyrolysis of a salt of a 3-oic acid of formula XXVI is the method described above wherein the salt of the 3-oic acid is heated in a liquid basic organic solvent. Especially preferred solvents for the pyrolysis of a salt of a compound of formula XXVI are triethanolamine and quinoline.

As indicated in the foregoing paragraph the pyrolysis of a salt of a compound of formula XXVI involves two separate chemical attacks; one being the elimination of the 11-leaving group and the other being the splitting off of the A-ring residue. Instead of effecting these two attacks simultaneously, as described above, it is also possible to effect them sequentially by just prior to formation of the salt, effecting elimination of the leaving group of the compound of formula XXVI. This elimination yields a $\Delta^{9(11)}$-seco acid of the formula

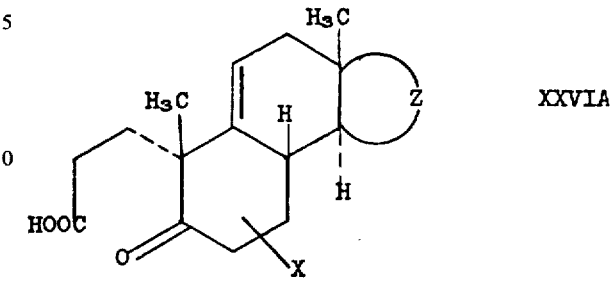

XXVIA wherein X and Z have the same meaning as above. The elimination can be effected by any conventional elimination means. It is suitably conducted under alkaline conditions in an anhydrous organic solvent. Preferably, it is effected by heating, i.e. at a temperature between about room temperature and the reflux temperature of the reaction mixture. Thus, treatment of a compound of formula XXVI with either an inorganic or organic acid or base results in the formation of the desired compound of formula XXVIA. Preferably a weak base is used, for example, a salt of a carboxylic acid (e.g. a lower alkanoic acid) with an alkali metal or an alkaline earth metal, for example, sodium acetate, potassium acetate, of the like. As indicated, the elimination is suitably conducted in an anhydrous organic solvent; suitable are solvents such as dilower alkyl-formamides, e.g. dimethylformamide, lower alkanoic acids, e.g. acetic acid, or the like. When a proton accepting solvent, such as dimethylformamide, is used, it itself can serve as the base for the purpose of this elimination reaction; i.e. if the solvent is basic then the elimination can be conducted without the addition of a separate basic material. Similarly, if the solvent is acidic, then the elimination can be conducted without the addition of a separate acidic material.

After the elimination is effected the $\Delta^{9(11)}$-seco acid product of formula XXVIA can then be converted to a salt, for example, an alkali metal salt, and the so-formed salt pyrolyzed according to the conditions described above for the pyrolysis of a compound of formula XXVI to compounds of formulas XII, XV and XVI.

After the above-described 11-leaving group elimination and A-ring residue splitting, conducted either simultaneously or sequentially, the desired desA-9-en-5-one -compounds of formulas XII, XV and XVI can be isolated by conventional means. However, is has been found particularly suitable with compounds of formulas XV and XVI to isolate by forming the disemicarbazone of the pyrolysis product and then regenerating therefrom the desired 5,20-dione of formulas XV or XVI, or if the 20-oxo group has been protected, for example, by reduction to a 20-hydroxy moiety, by forming the semicarbazone at the 5-position and then regenerating therefrom the desired 5-one compound.

In yet another embodiment of this invention starting material 11-hydroxy steroids of formula XXIV can be directly subjected to an oxidative ring opening of the A-ring by ozonolysis or treatment with hydroxide peroxide, as described above for the oxidative ring opening of the A-ring of a compound of formula XVII to a compound of formula XVIII. This oxidative ring opening of the A-ring of a compound of formula XXIV yeilds an 11-hydroxy-5-oxo-3,5-seco-A-norandrostan-5-oic acid 3,11-lactone or an 11-hydroxy-3-oxo-3,5-seco-A-norpregnan-3-oic acid 3,11-lactone of the formula

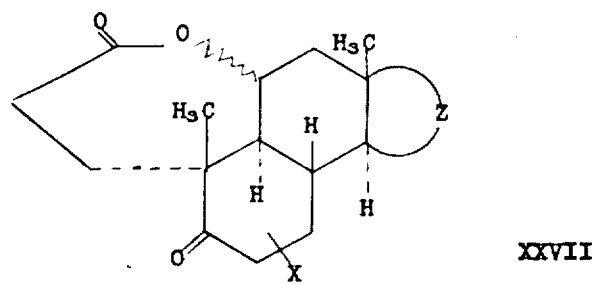

XXVII wherein X and Z have the same meaning as above. Treatment of the 3,11-lactone of formula XXVII with an alkali metal hydroxide such as sodium hydroxide gives the salt of the same keto acid. Without isolation, this salt can then be subjected to pyrolysis yielding a mixture of an 11-hydroxy-10αdesA-androstan-5-one and an 11-hydroxy-10β-desA-androstan-5-one or a mixture of an 11-hydroxy-10α-desA-pregnan-5-one and an 11-hydroxy-10β-desA-pregnan-5-one, as illustrated below:

wherein in formulas XXVIII and XXIX, XX and Z have the same meaning as above.

This pyrolysis of an alkali metal salt derived from a compound of formula XXVII can be effected under the same conditions as described above for the pyrolysis of a compound of formula XVIII to compounds of the formulae XIX and XX. Though either the 10β-compound of formula XXVIII or the 10α-compound of formula XXIX can be subjected to the subsequent steps of this reaction sequence, it is suitable to utilize the 10β-compound of formula XXVIII. Conversion of the 10α-compound of formula XXIX to the 10β-compound of formula XXVIII can be effected under the same conditions as described above for the conversion of the compound of formula XX to a compound of formula XIX.

In the next step of this reaction sequence, the 11-hydroxy compound of formula XXVIII or of formula XXIX can be subjected to esterification whereby to convert the 11-hydroxy group to a leaving group in the 11-position. This esterification can be effected with the same acids or acid derivatives and in the same manner as described above for the esterification of a compound of formula XXIV to a compound of formula XXV. As in that instance, it is also preferred in the present instance to form a mesoxy leaving group in the 11-position, though, of course, other leaving groups as described above are useful for the instant purpose. There is thus obtained a compound of the formula

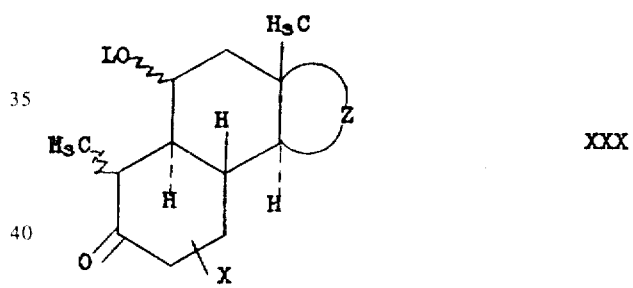

XXX wherein X, Z and LO have the same meanings as above.

The leaving group can then be eliminated from the 11-position of a compound of formula XXX resulting in a direct formation of a desA-androst-9-en-5-one or a desA-pregn-9-en-5-one of formulae XII, XV, XVI. This elimination can be effected by any conventional elimi- XXVII
↓
alkali metal salt

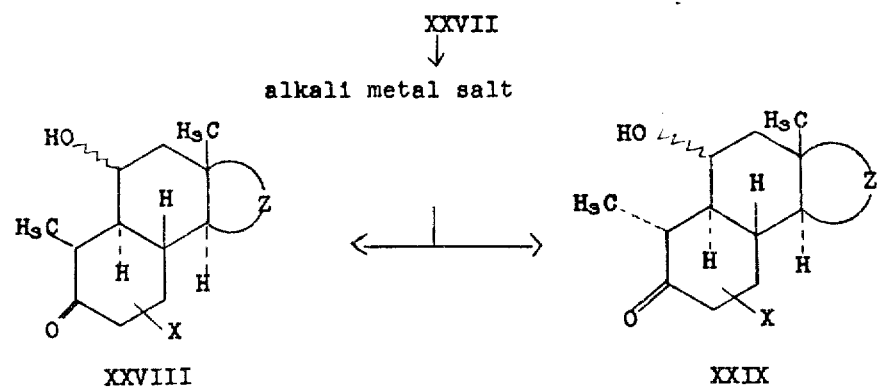

XXVIII          XXIX nation means. It is suitably conducted under alkaline conditions in an anhydrous organic solvent. Preferably, it is effected by heating, i.e. at a temperature between about room temperature and the reflux temperature of the reaction mixture. Thus, treatment of a compound of formula XXX with either an inorganic or organic base results in the formation of the desired compound of formulae XII, XV, XVI. Preferably a weak base is used, for example, a salt of a carboxylic acid (e.g. a lower alkanoic acid) with an alkali metal or an alkaline earth metal, for example, sodium acetate, potassium acetate, or the like. As indicated, the elimination is suitably conducted in an anhydrous organic solvent; suitable are solvents such as dilower alkyl-formamides, e.g. dimethyl formamide, lower alkanoic acids, e.g. acetic acid, or the like. When a proton accepting solvent, such as dimethyl formamide, is used, it itself can serve as the base for the purpose of this elimination reaction; i.e. if the solvent is basic then the elimination can be conducted without the addition of a separate basic material.

In another aspect, compounds of Formula XXX can be prepared from compounds of the formula

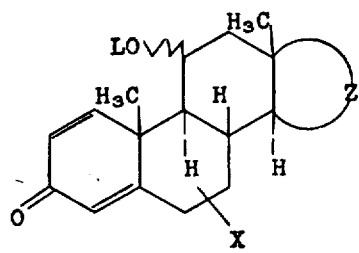

XXXA wherein X, Z and LO have the same meanings as above.

The compounds of formula XXXA can be prepared from corresponding 11-hydroxy compounds by esterification as described above for the preparation of compounds of formula XXV from compounds of formula XXIV. The compounds of formula XXX can be prepared from compounds of formula XXXA in the same member that compounds of formula XXX are prepared from compounds of formula XXV, i.e. by oxidative ring opening of the A-ring of a compound of formula XXXA followed by elimination of the residue of the A-ring to yield a compound of formula XXX. The oxidative ring opening of the compounds of formula XXXA can be performed by ozonolysis as described above for conversion of a compound of formula XXV to a compound of formula XXVI. Such ozonolysis of a compound of formula XXXA yields a compound of the formula

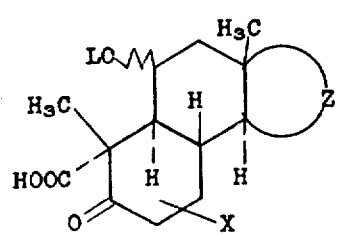

XXXB wherein X, Z and LO have the same meaning as above.

A compound of formula XXXB can then be converted to a compound of formula XXX. This removal of the residue of the A-ring, i.e. decarboxylation, can be effected as described above for the conversion of a compound of formula XIXB to a compound of formula XIX.

The compounds of formulae I–V preparable by the methods of this invention are not only pharmaceutically useful compounds as described above, but also are themselves useful as intermediates for other 9β,10α-steroids; for example, compounds wherein X is hydrogen or lower alkyl can be modified so as to introduce unsaturation between C-6 and C-7. This can be effected by dehydrogenation means, for example, by halogenation followed by dehydrohalogenation or by means of 2,3-dichloro-5,6-dicyanobenzoquinone, according to known methods. Thus, for example, a 9β,10α-progesterone of formula IV wherein X is hydrogen or lower alkyl can be converted to a 9β,10α-pregna-4,6-dien-3,20 -dione.

A further embodiment of this invention comprises the preparation of 9β,10α-steroids of formulae I–V containing an 11-hydroxy substituent. This can be effected by utilizing an 11-hydroxy-10β-desA-androstan-5-one or 11-hydroxy-10α-desA-pregnan-5-one of formula XXIX or an 11-hydroxy-10β-desA-androstan-5-one or 11-hydroxy-10β-desA-pregnan-5-one of formula XXVIII as the starting materials. It is preferred in this embodiment to use the 10β-isomers of formula XXVIII as starting materials. As a first step in this the 11-hydroxy group of the compound of formulae XXVIII or XXIX should be protected. This is suitably effected by esterification, preferably with a carboxylic acid, for example, a lower alkanoic acid such as acetic acid, benzoic acid, or the like. Conversion of the so-obtained 11-esterified hydroxy compound then yields an 11-(esterified hydroxy)-desA-androst-9-en-5-one (i.e. a compound of formula XII containing an 11-esterified hydroxy moiety) or an 11-esterified hydroxy-desA-pregn-9-en-5-one (i.e. a compound of formulae XV-XVI containing an 11α-esterified hydroxy moiety). This conversion can be effected by halogenation followed by dehydrohalogenation, as described above for the conversion of a compound of formulae XIX or XX to a compound of formulae XII, XV or XVI. Catalytic hydrogenation of the so-obtained compound of the formula

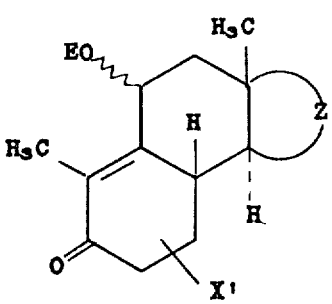

XXXI wherein X' and Z have the same meaning as above, and EO is an esterified hydroxy group as described above in this paragraph, yields an 11-esterified hydroxy-desA-9β, 10β-androstan-5-one or 11-esterified hydroxy-desA-9β,10β-pregnan-5-one, of the formula

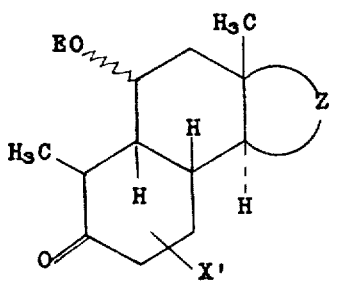

XXXII wherein X', Z and EO have the same meaning as above.

This hydrogenation can be conducted in the same manner as described above for the hydrogenation of a compound of formulae XII–XVI to a compound of formulae VII, X, XI. Also, compounds of formula XXXII containing a 17-oxo moiety can be converted to a corresponding compound containing a 17β-hydroxy, 17α-lower alkenyl or lower alkynyl moiety by the methods described above. Also, compounds of formula XXXII can be hydrolyzed to yield corresponding 11-hydroxy compounds of formula XXXII, i.e. wherein EO is hydroxy.

Condensation of the so-obtained compound of formula XXXII or the corresponding 17β-hydroxy, 17α-lower alkenyl or lower alkynyl compound (i.e. a compound of formula VI containing a free or 11-esterified hydroxy group) then yields the desired end-product 9β, 10α-steroid of formulae I–V containing an 11-hydroxy group. Such condensation can be effected as described above for the preparation of a compound of formulae I–V from a compound of formulae VI–XI. The so-obtained 9β, 10α-steroids containing an 11-esterified hydroxy group can be hydrolyzed to the corresponding compounds containing an 11-hydroxy group, which latter compounds are themselves useful as intermediates, for example, the 11-hydroxy group can be oxidized by methods known per se to yield corresponding 11-oxo steroids analogous to compounds of formulas I–V.

The pharmaceutically useful compounds prepared by the methods of this invention can be administered internally, for example, orally or parenterally, with dosage adjusted to individual requirements. They can be administered in conventional pharmaceutical forms, e.g. capsules, tablets, suspensions, solutions, or the like.

The following examples are illustrative but not limitative of this invention. All temperatures are in degrees Centigrade. The Florisil adsorbent used infra is a synthetic magnesia-silica gel available from the Floridin Company, P. O. Box 989, Tallahassee, Flor. (cf. p. 1590, Merck Index, 7th Edition, 1960). 100–200 mesh material was used. The moiety designated by tetrahydropyranyloxy is tetrahydro-2-pyranyloxy. When it is stated that a precedure is effected in the cold, it should be understood that it is commenced at 0°C. Throughout this application when compounds of the pregnane series are referred to it should be understood that it is compounds of the 17β-pregnane series that are being referred to, unless specifically indicated to the contrary, and whether or not the compound of the pregnane series is specifically indicated as of the 17β-series.

EXAMPLE 1

A solution of 3.2 g. of 17α-ethyltestosterone in 50 ml. methylene chloride and 25 ml. ethyl acetate was ozonized at −70° (acetone-dry ice bath) until the solution was blue in color. After oxygen was passed through, the solution was evaporated at room temperature in vacuo. The syrupy residue was then dissolved in 100 ml. of glacial acetic acid, and after addition of 5 ml. of 30 per cent hydrogen peroxide, left for 24 hours at 0°–5°. Following this time, it was evaporated to dryness, dissolved in 1500 ml. ether, and extracted with 2N sodium carbonate solution. The alkaline extract was poured in ice cold hydrochloric acid. The resultant crystalline 17α-ethyl-17β-hydroxy-5-oxo-3,5-seco-A-norandrostan-3-oic acid was filtered, washed with water and dried. Upon being recrystallized from acetone, it melted at 196°–197°.

EXAMPLE 2

A solution of 1.5 g. of 17α-ethyl-17β-hydroxy-5-oxo-3,5-seco-A-norandrostan-3-oic acid in 100 ml. of methanol was titrated with 2N sodium methoxide to the reddish color of phenolphthaleine, and then evaporated to dryness in vacuo, giving as the residue, the sodium salt of 17α-ethyl-17β-hydroxy-5-oxo-3,5-seco-A-norandrostan-3-oic acid. 5 g. of sodium-phenylacetate was added to the residue, and the mixture pyrolyzed in vacuo (<0.1 mm) at 285°–295°, for 2.5 hours. The sublimate was dissolved in acetone, filtered and the filtrate concentrated in vacuo. The resultant syrupy residue was chromatographed on a 60 g. Florisil (adsorbent) column. The fractions eluted with benzene and 0.5 per cent ethylacetate in benzene were combined and gave 17α-ethyl-17β-hydroxy-10α-desA-androstan-5-one, m.p. 94°–95° after recrystallization from petroleum ether. The fractions eluted with 2 per cent and 5 per cent ethylacetate in benzene were combined and gave 17α-ethyl-17β-hydroxy-10β-desA-androstan-5-one, m.p. 185°–185.5°, recrystallizations two recrystallization from petroleum ether.

EXAMPLE 2a

To a solution of 100 mg. of 17α-ethyl-17β-hydroxy-10β-desA-androstan-5-one in 10 ml. of absolute ethanol was added one equivalent of sodium ethoxide dissolved in 5 ml. of absolute ethanol. This reaction mixture was maintained at room temperature overnight, then acidified with glacial acetic acid, poured in water and extracted with methylene chloride. The extract was washed with water, dried over anhydrous sodium sulfate and concentrated in vacuo. Thin layer chromatography showed the product to be 17α-ethyl-17β-hydroxy-10α-desA-androstan-5-one. It was obtained crystalline from petroleum ether-ether and melted at 89°–95°.

EXAMPLE 3

1.13 g. of 17α-ethyl-17β-hydroxy-10α-desA-androstan-5-one was dissolved in 120 ml. of anhydrous ether (or 1.13 g. of 10β-isomer was dissolved in 300 ml. of anhydrous ether), and after cooling in a salt-ice bath, several drops of 30 per cent hydrobromic acid in acetic acid were added. This was followed by the dropwise addition during five minutes of 0.684 g. of bromine dissolved in 2 ml. of acetic acid. This addition was synchronized with the decoloration rate of the reaction mixture. Immediately after this, 5 ml. of a saturated solution of sodium bisulfite and 5 ml. of 2N sodium carbonate solution were added. The mixture was then transferred into a separatory funnel, 500 ml. of ether added, shaken and separated. The ether part was washed with water, dried and evaporated. The resultant bromides were dissolved in 100 ml. of dimethylformamide, and after addition of 3 g. of lithium carbonate, the solution was heated at 100° for 45 minutes. After cooling, it was poured into one liter of ether, washed with water, 1N hydrochloric acid, 2N sodium carbonate, water, dried and evaporated. The residue was dissolved in 40 ml. of glacial acetic acid, 1.2 g. of sodium acetate and 1.2 g. of zinc powder added, and the so-formed mixture heated 10 minutes at 80°. It was then poured into one liter of ethylacetate and the resultant solution washed with saturated sodium bicarbonate, then with water, dried and evaporated. The residue was chromatographed on Florisil (adsorbent)column. The fraction with benzene and ½ per cent ethylacetate in benzene gave regenerated starting material. Fractions with 1 and 2 per cent ethylacetate in benzene gave 17α-ethyl-17β-hydroxy-desA-androst-9-en-5-one, which after sublimation (140° and 0.1 mm. Hg vacuum), was obtained as a glass. $[\alpha]_D^{25}$ −36.6° (c = 1, $CHCl_3$).

EXAMPLE 4

A suspension of 262 mg. of 5 per cent rhodium on alumina catalyst in a mixture of 26 ml. of 95 per cent ethanol and 5.25 ml. of 2N sodium hydroxide solution was pre-reduced, (i.e. hydrogenated at room temperature and atmospheric pressure). To this was added a solution of 262 mg. of 17α-ethyl-17β-hydroxy-desA-androst-9-en-5-one in 15 ml. of 95 per cent ethanol, and the mixture then hydrogenated at atmospheric pressure and room temperature. After one mole-equivalent of hydrogen was absorbed, the reaction was stopped, the catalyst was separated by filtration, and the filtrate evaporated in vacuo. Glacial acetic acid (1 ml.) was added to the residue, which was then dissolved in 1 liter of ether. The cloudy solution which resulted was washed with 2N $Na_2CO_3$ solution, then with water, dried and evaporated to dryness in vacuo.

The reaction was repeated 3 more times, and the combined products chromotographed on a Florisil (adsorbent) column. The eluates with 1 per cent ethyl acetate in benzene gave first crystalline fractions, which were followed by non-crystalline fractions. The non-crystalline fractions were dissolved in 100 ml. of methylene chloride, and after the addition of 2.5 ml. of 2 per cent $CrO_3$ in 90 per cent acetic acid, stirred overnight. The excess of chromic acid was removed by washing the methylene chloride solution with 10 ml. of 10 per cent sodium hydrogen sulfite solution, following by washing with 2N $Na_2CO_3$ solution and then with water. It was then dried and evaporated in vacuo. The residue was dissolved in 50 ml. of anhydrous ethanol containing 172 mg. of sodium ethoxide, and left overnight. The next day, after addition of 0.5 ml. of glacial acetic acid, the solution was evaporated in vacuo, and the residue was taken up in 1 liter of ether. The ether solution was washed with 2N $Na_2CO_3$ solution, then with water, dried and evaporated. The residue was chromatographed on Florisil (adsorbent) column and gave crystalline 17α-ethyl-17β-hydroxy-desA-9β,10β-androstan-5-one identical (by thin layer chromatography) with the crystalline material obtained in the first chromatographic separation. After two recrystallizations from ether, it melted at 142°–144°; $[\alpha]_D^{25}$ −11.65° [methanol, c = 1.245 per cent].

EXAMPLE 5

To a solution of 132 mg. of 17α-ethyl-17β-hydroxy-desA-9β,10β-androstan-5-one in 12.5 ml. of absolute ethanol containing 34 mg. of sodium ethoxide, 0.15 ml. of freshly distilled methylvinyl ketone was added. The reaction mixture was then refluxed for two hours in a nitrogen atmosphere. After cooling the reaction mixture, 0.1 ml. of glacial acetic acid was added thereto and the resulting mixture was then poured into 1 liter of ether. The resultant ether solution was washed with water, dried over anhydrous sodium sulfate and evaporated in vacuo. The residue was chromatographed on fluorescent silica-gel plates, with the solvent system, 60 per cent ethyl acetate-40 per cent heptane. The fluorescent part of the layers was extracted with ethyl acetate. The residue obtained after evaporation of ethyl acetae was first crystallized from ether-petroleum ether, then a second time from pure ether, yielding 17β-ethyl-9β,10α-testosterone, m.p. 131°–135°.

EXAMPLE 6

A solution of 6.4 g. of 11α-hydroxy-progesterone in 100 ml. of ethylacetate and 50 ml. of methylene chloride was treated with ozone at −70° until the solution became blue in color. Oxygen was then passed through and the solution evaporated at room temperature in vacuo. The so-obtained syrupy residue was dissolved in 100 ml. of glacial acetic acid, and after the addition of 5 ml. of 30 per cent hydrogen peroxide, left for 24 hours at 2° (in an ice box). The solution was then evaporated in vacuo, and the residue triturated with ether yielding crystals. Recrystallization from acetone yielded 11α-hydroxy-3,5-seco-A-nor-pregnane-5,20-dione-3-oic acid 3,11-lactone, m.p. 253°–256°. $[\alpha]_D^{25}$ +193.3° (c = 1, in chloroform).

EXAMPLE 7

A methanolic solution of 7.5 g. of 11α-hydroxy-3,5-seco-A-nor-pregnane-5,20-dione-3-oic acid 3,11-lactone was treated with one equivalent of 10N sodium hydroxide solution and then evaporated to dryness. Sodium phenylacetate (26 g.) was added to the so-obtained sodium salt and the mixture pyrolyzed at 295° for two hours in vacuo. The crude sublimate was chromatographed on a silica-gel column and eluted with 10 per cent ethylacetate in benzene. The amorphous solid 11α-hydroxy-10α-desA-pregnane-5,20-dione was first eluted from the column. IR-spectrum in chloroform: 3620 and 3600 $cm^{-1}$ (—OH); 1706 $cm^{-1}$ (carbonyl group). NMR-spectrum in deuterochloroform: a doublet for 10α-$CH_3$ at 73.5 and 80.5 c.p.s., downfield from TMS at 60 Mc/sec. Further elution of the column with 10 per cent ethylacetate in benzene yielded crystalline 11α-hydroxy-10β-desA-pregnane-5,20-dione which was recrystallized from methylene chloride-petroleum ether, m.p. 150°–152°; $[\alpha]_D^{25}$ +84.0° (c = 0.5 in absolute ethanol).

EXAMPLE 8

To a solution of 100 mg. of methanesulfonylchloride in 0.7 ml. of pyridine, there was added 100 mg. of 11α-hydroxy-10β-desA-pregnane-5,20-dione. The mixture was then allowed to stand overnight at 2° (in a refrigerator), then was diluted with water (100 ml.) and extracted with chloroform (3 × 150 ml.) and methylene chloride (100 ml.). The combined organic extracts were washed with water, 1N hydrochloric acid and again with water, then dried over anhydrous sodium sulfate and evaporated in vacuo. The crystalline residue was recrystallized from ether, giving 11α-hydroxy-10β-desA-pregnane-5,20-dione methanesulfonate, m.p. 139°–140°; $[\alpha]_D^{25}$ +46° (c = 0.5 in absolute ethanol).

EXAMPLE 9

A solution of 200 mg. of 11α-hydroxy-10β-desA-pregnane-5,20-dione methanesulfonate in 50 ml. of dimethylformamide was refluxed for eight hours and then evaporated to dryness. The residue was chromatographed on a Florisil (adsorbent) column. Elution with 2 per cent ethylacetate/benzene and evaporation of the eluant yielded desA-pregn-9-ene-5,20-dione in the form of colorless needles, m.p. 111°–113°. It was shown by mixed melting point to be identical with a sample of the same compound prepared as described in Example 12.

EXAMPLE 10

To a solution of 20 g. of 11α-hydroxy-progesterone in 150 ml. of pyridine maintained at 0°, there was added 6 ml. of methanesulfonylchloride, and the reaction mixture allowed to stand overnight at 0°. It was then diluted with a large excess of water and extracted with chloroform. The organic extracts were washed with 2N hydrochloric acid and water, then dried over anhydrous sodium sulfate and evaporated in vacuo. The solid residue was recrystallized from methanol to give 11α-mesyloxy-progesterone, m.p. 159.5°–160°; $[\alpha]_D^{25}$ +145.6 (c = 1, chloroform).

EXAMPLE 11

A solution of 12 g. of 11α-mesyloxy-progesterone in 300 ml. of methylene chloride/ethyl acetate (2:1) was treated with ozone at −70° until the solution became blue in color. The excess of ozone was removed by bubbling oxygen through the reaction mixture for five minutes. Methylene chloride was then removed under reduced pressure, and the solution diluted with ethyl acetate to 200 ml. After addition of 12 ml. of 30 per cent aqueous hydrogen peroxide, the reaction mixture was then allowed to stand overnight at 2° (i.e., in the refrigerator), then evaporated to a volume of 75 ml. and diluted with 125 ml. of benzene. The aqueous solution, obtained by extraction with 8 portions of 75 ml. 2N sodium carbonate followed by combining the aqueous extracts was acidified with cold concentrated hydrochloric acid to pH 2 and extracted with methylene chloride. This extract was dried over anhydrous sodium sulfate and evaporated in vacuo in dryness. The residue crystallized when triturated with ether-acetone mixture, yielding crude 11α-mesoxy-5,20-dioxo-3,5-seco-A-nor-pregnan-3-oic acid. After recrystallization from acetone-petroleum ether, m.p. 152°–153°; $[\alpha]_D^{25}$ +47.9° (c = 1, chloroform).

EXAMPLE 12

A solution of 6 g. of 11α-mesoxy-5,20-dioxo-3,5-seco-A-nor-pregnan-3-oic acid in 150 ml. of methanol was mixed with a solution of 1.5 g. of sodium carbonate in 55 ml. of water. The mixture was then transferred into a 1 liter sublimation flask, and evaporated to dryness. To the thus formed sodium salt, 20 g. of sodium phenyl acetate is added, and after closing the top part of the apparatus, this mixture was pyrolyzed at 290° and 0.02 mm. for four hours. The product, which collects on the cold finger, was dissolved in ether and filtered. The filtrate was then evaporated to dryness. Purification of the residue by chromatography on a 40 g. silica-gel column (benzene eluant) gave crystalline desA-pregn-9-ene-5,20-dione; m.p. 111°–113° (after recrystallization from ether). $[\alpha]_D^{25}$ +56.8° (c = 0.25 per cent in methanol).

EXAMPLE 13

To a solution of 1.2 g. of desA-pregn-9-ene-5,20-dione in 20 ml. of methanol maintained at 0°, there was slowly added a cooled solution of 1.2 g. of sodium borohydride in 22 ml. methanol, and the resultant mixture was left for 72 hours at 0°. It was then diluted with 100 ml. of water and extracted with four 100 ml. portions of chloroform. The extract was dried over anhydrous sodium sulfate and evaporated in vacuo, yielding a colorless oily product. This product was dissolved in 250 ml. of chloroform and 6 g. of manganese dioxide was added to the solution which was then stirred for 72 hours at room temperature, filtered and the filtrate evaporated to dryness in vacuo. The residue was chromatographed on a silica-gel column and the eluates with 5 per cent ethyl acetate in benzene, after concentration gave crystalline 20β-hydroxy-desA-pregn-9-en-5-one which upon recrystallization from methylene chloride-petroleum ether formed colorless needles, m.p. 122°–123°; $[\alpha]_D^{25}$ −33° (c = 0.5, absolute ethanol).

EXAMPLE 14

A suspension of 262 mg. of 5 per cent rhodium on alumina catalyst in a mixture of 26 ml. of 95 per cent ethanol and 5.25 ml. of 2N aqueous sodium hydroxide was hydrogenated at room temperature and atmospheric pressure. To this was added a solution of 262 mg. of 20β-hydroxy-desA-pregn-9-en-5-one in 15 ml. of 95 per cent ethanol, and the reaction mixture then hydrogenated at room temperature and atmospheric pressure. After one mole equivalent of hydrogen was absorbed, the reaction was stopped, and the catalyst was separated by filtration. After standing overnight the filtrate was concentrated in vacuo. To the residue was added 1 ml. of glacial acetic acid, and it was then dissolved in 1 liter of ether. The cloudy solution was washed with 2N aqueous sodium carbonate solution, then with water, then dried over anhydrous sodium sulfate and evaporated to dryness in vacuo. It yielded a colorless oil, which was chromatographed on a silica-gel column using 1 per cent ethyl acetate in benzene as the elutant. First eluted was 20β-hydroxy-10α-desA-pregnan-5-one, m.p. 107°–108° after recrystallization from methylene chloride/petroleum ether. R.D. (in methanol); $[\alpha]_{500}$ −25.3°, −$[\alpha]_{400}$ −89°; $[\alpha]_{350}$ −274°; $[\alpha]_{305}$ −1335°; $[\alpha]_{300}$ −1165°.

Further elution yielded 20β-hydroxy-9β,10β-desA-pregnan-5-one as a colorless oil. R. D. (in methanol); $[\alpha]_{500}$ −14.8°; $[\alpha]_{400}$ −4.4°; $[\alpha]_{350}$ +22.2°; $[\alpha]_{310}$ +2148°.

EXAMPLE 15

A suspension of 262 mg. of 5 per cent rhodium on alumina catalyst in a mixture of 2 ml. of 3N aqueous hydrochloric acid and 18 ml. 95 per cent ethanol was hydrogenated at room temperature and atmospheric pressure. A solution of 262 mg. of 20β-hydroxy-desA-pregn-9-en-5-one in 5 ml. of absolute ethanol was introduced into the hydrogenation flask, and the reaction mixture was then hydrogenated at room temperature and atmospheric pressure. After one mole-equivalent of hydrogen was absorbed, the reaction was stopped, the catalyst was separated by filtration, and the filtrate neutralized with 2N aqueous sodium hydroxide solution. An excess of 5 ml. of 2N aqueous sodium hydroxide was added and the solution allowed to stand overnight. Ethanol was then removed by evaporation at reduced pressure, and after addition of 1 ml. of glacial acetic acid, it was extracted with 1 liter of ether. The extract was washed with 2N aqueous sodium carbonate solution, then with water, dried and concentrated in vacuo. It gave a colorless oil, which was chromatographed on a silica-gel column using 2 per cent ethyl acetate in benzene as the elutant. The first fractions of the eluate yielded, upon concentration, 20β-hydroxy-10α-desA-pregnan-5-one. From the immediately subsequent fraction, 20β-hydroxy-9β,10β-desA-pregnan-5-one was obtained. Both products were identical with the same compounds obtained in Example 14.

EXAMPLE 16

20β-Hydroxy-9β,10α-pregn-4-en-3-one is prepared by condensation of 20β-hydroxy-9β,10β-desA-pregnan-5-one with methyl vinyl ketone according to the procedure of Example 5. The product melts at 176.5°–178.5°; $[\alpha]_D^{25}$ —143° (chloroform).

EXAMPLE 17

A medium is prepared of 20 g. of Edamine enzymatic digest of lactalbumin, 3 g. of corn steep liquor and 50 g. of technical dextrose diluted to 1 liter with tap water and adjusted to a pH of 4.3 – 4.5. Twelve liters of this sterilized medium is inoculated with Rhizopus nigricans minus strain (A.T.C.C. 6227b) and incubated for 24 hours at 28° using a rate of aeration and stirring such that the oxygen uptake is 6.3 14 7 millimoles per hour per liter of $Na_2SO_3$ according to the method of Cooper et al, Ind. Eng. Chem., 36, 504 (1944). To this medium containing a 24 hour growth of Rhizopus nigricans minus strain, 6 g. of 17α-acetoxy-progesterone in 150 ml. of acetone is added. The resultant suspension of the steroid in the culture is incubated under the same conditions of temperature and aeration for an additional 24 hour period after which the beer and mycelium are extracted. The mycelium is then filtered, washed twice, each time with a volume of acetone approximately equal in volume to the mycelium, extracted twice, each time with a volume of methylene chloride approximately equal to the volume of the mycelium. The acetone and methylene chloride extracts including solvent are then added to the beer filtrate. The mixed extracts and beer filtrate are then extracted successively with 2 portions of methylene chloride, each portion being one-half the volume of the mixed extracts and beer filtrate, and then with 2 portions of methylene chloride, each portion being ¼ the volume of the mixed extracts and beer filtrate. The combined methylene chloride extracts are then washed with 2 portions of a 2 per cent aqueous solution of sodium bicarbonate, each portion being 1/10 the volume of the combined methylene chloride extracts. The methylene chloride extracts are then dried with about 3 – 5 g. of anhydrous sodium sulfate per liter of solvent, and then filtered. The solvent is then removed from the filtrate by distillation, and the residue is dissolved in a minimum of methylene chloride, filtered and the solvent evaporated from the filtrate. The resulting crystals are then dried and washed five times, each time with a 5 ml. portion of ether per gram of crystal. The crystals are then recrystallized from ether giving 17α-acetoxy-11α-hydroxy-progesterone. 17α-acetoxy-11α-mesoxy-progesterone is prepared by treatment of 17α-acetoxy-11α-hydroxy-progesterone with methanesulfonyl chloride, according to the procedure of Example 10.

EXAMPLE 18

17α-Acetoxy-5,20 -dioxo-11α-mesoxy-A-nor-3,5-seco-pregnan-3-oic acid is prepared by ozonolysis of 17α-acetoxy-11α-mesoxy-progesterone, according to the procedure of Example 11.

EXAMPLE 19

17α-Acetoxy-desA-pregn-9-ene-5,20-dione is prepared from 17α-acetoxy-5,20-dioxo-11α-mesoxy-A-nor-3,5-seco-pregnan-3-oic acid by conversion of the latter to its sodium salt followed by pyrolysis, according to the procedure of Example 12.

EXAMPLE 20

17α-Acetoxy-20β-hydroxy-desA-pregn-9-en-5-one is prepared from 17α-acetoxy-desA-pregn-9-en-5,20-dione by reduction and reoxidation according to the procedure of Example 13.

EXAMPLE 21

17α-Acetoxy-20β-hydroxy-9β,10β-desA-pregnan-5-one is prepared from 17α-acetoxy-20β-hydroxy-desA-pregn-9-en-5-one by hydrogenation under acidic conditions in the presence of a rhodium catalyst, according to the procedure of Example 15.

EXAMPLE 22

17α-Acetoxy-20β-hydroxy-9β,10α-pregn-4-en-3-one is prepared by condensing methyl vinyl ketone with 17α-acetoxy-20β-hydroxy-9β,10β-desA-pregnan-5-one according to the procedure of Example 5 except instead of conducting the condensation in absolute ethanol and catalyzing it with sodium ethoxide, the condensation is conducted in acetic acid and is catalyzed with p-toluene solfonic acid.

EXAMPLE 23

20β-Hydroxy-4-methyl-9β,10α-pregn-4-en-3-one is prepared by condensing 20β-hydroxy-9β,10β-desA-pregnan-5-one and ethyl vinyl ketone according to the procedure of Example 5.

EXAMPLE 24

17β-Hydroxy-5-oxo-3,5-seco-A-nor-androstan-3-oic acid is prepared by ozonolysis of testosterone according to the procedure of Example 1.

EXAMPLE 25

17β-Hydroxy-10α-desA-androstan-5-one and 17β-hydroxy-10β-desA-androstan-5-one are prepared from 17β-hydroxy-5-oxo-3,5-seco-A-norandrostan-3-oic acid by conversion of the latter to its sodium salt followed by pyrolysis, according to the procedure of Example 2.

EXAMPLE 26

17β-Hydroxy-desA-androst-9-en-5-one is prepared from 17β-hydroxy-10α-desA-androstan-5-one by bromination followed by dehydrobromination, according to the procedure of Example 3.

EXAMPLE 26a

DesA-androst-9-ene-5,17-dione is prepared from 17β-hydroxy-desA-androst-9-en-5-one by oxidation of the latter with a 2 per cent chromic acid solution in 90 per cent acetic acid. The so-obtained desA-androst-9-ene-5,17-dione is recrystallized from cyclohexane and melts at 123°–123.5°; $[\alpha]_{5\kappa9}^{25} = +83°$ (c = 0.1021, dioxane).

EXAMPLE 27

A solution of 236 mg. of 17β-hydroxy-desA-androst-9-en-5-one in 40 ml. 95 per cent ethanol and 5.25 ml. 2N aqueous sodium hydroxide solution was hydrogenated with one mole equivalent of hydrogen over 236 mg. of prereduced 5 per cent rhodium on alumina catalyst. After separation of catalyst, the solution was concentrated in vacuo to dryness, and the residue taken up in one liter of ether. The ether solution was washed with water, dried over anhydrous sodium sulfate and evaporated to dryness in vacuo. From the residue 17β-hydroxy-9β,10β-desA-androstan-5-one was obtained by crystallization. M.p. 144.5°–145°; $[\alpha]_D^{25} -22°$ (c = 0.103; dioxane). The 17β-acetate (i.e., 17β-acetoxy-962 ,10β-desA-androstan-5-one) is obtained by acetylation of testosterone followed by ozonolysis, pyrolysis, bromination and dehydrobromination, and reduction according to the method of Examples 24, 25, 26 and 27 respectively, and melts at 118°–119°; $[\alpha]_D^{25} -28°$ (c = 0.103; dioxane).

EXAMPLE 28

A solution of 238 mg. of 17β-hydroxy-9β,10β-desA-androstan-5-one, 1 ml. of ethylene glycol and catalytic amount of p-toluene sulfonic acid in 100 ml. of anhydrous benzene was slowly distilled until no more water was coming over. The solution was then concentrated in vacuo to a small volume, and 17β-hydroxy-9β,10β-desA-androstan-5-one 5-ethylene ketal was obtained from the residue by crystallization. M. p. 115°–116°; $[\alpha]_D^{25} -9°$ (c = 0.0987; dioxane).

EXAMPLE 29

To a solution of 282 mg. of 17β-hydroxy-9β,10β-desA-androstan-5-one 5-ethylene ketal in 50 ml. of methylene chloride was added 1 equivalent of 2 per cent chromic acid in pyridine, and the reaction mixture then stirred overnight. The reaction mixture was then washed with 10 per cent aqueous sodium hydrogen sulfite, 2N aqueous sodium carbonate, water, then dried over anhydrous sodium sulfate and concentrated in vacuo to dryness. Crystallization of the residue gave 9β,10β-desA-androstane-5,17-dione 5-monoethylene ketal. Splitting of the ketal in acetone solution in the presence of a catalytic amount of p-toluene sulfonic acid gives 9β,10β-desA-androstane-5,17-dione which melts, after recrystallization from cyclohexane, at 77.5°–78°; $[\alpha]_D25 +55°$ (c = 0.107; dioxane).

EXAMPLE 30

To a preformed solution of one mole equivalent of prop-1'-inyl lithium in 100 ml. of anhydrous liquid ammonia was added tetrahydrofuran solution of 200 mg. of 9β,10β-desA-androstane-5,17-dione 5-monoethylene ketal, and the reaction mixture stirred for two hours. After addition of one gram of ammonium chloride, cooling was discontinued, and the reaction mixture allowed to evaporate. The residue was extracted with methylene chloride, the extract was washed with water, dried over anhydrous sodium sulfate and evaporated. The residue was dissolved in 20 ml. of acetone and the catalytic amount of p-toluenesulfonic acid added, and the solution was refluxed for two hoours, then poured in water and extracted in methylene chloride. The methylene chloride extract was washed with water, then dried over anhydrous sodium sulfate and evaporated to dryness in vacuo. Crystallization of the residue gave 17α-(prop-1'-inyl)-17β-hydroxy-9β,10β-desA-androstan-5-one.

EXAMPLE 31

17α-(prop-1'-inyl)-17β-hydroxy-9β,10α-androstan-4-en-3-one is prepared by condensing methyl vinyl ketone with 17α-(prop-1'-inyl)-17β-hydroxy-9β,10β-desA-androstan-5-one according to the procedure of Example 5. The product melts at 164°–165°.

EXAMPLE 32

To a stirred solution of one mole equivalent of 2-methylprop-2-enyl magnesium bromide in 100 ml. of ether at room temperature was added dropwise a solution of 280 mg. of 9β,10β-desA-androstane-5,17-dione 5-mono-ethylene ketal in 100 ml. of tetrahydrofuran. The reaction mixture was refluxed for one hour. After cooling in an ice-salt bath, a saturated solution of sodium sulfate was slowly added to decompose the Grignard complex. This was followed by addition of anhydrous sodium sulfate. The solution was separated by filtration and concentrated in vacuo to dryness. The solution of the residue and of a catalytic amount of p-toluene sulfonic acid in 20 ml. of acetone was refluxed for two hours, then poured in water and extracted in methylene chloride. Methylene chloride extract was washed with water, dried over anhydrous sodium sulfate and evaporated to dryness. From the residue 17α-(2'-methyl-prop-2'-enyl)-17β-hydroxy-9β,10β-desA-androstan-5-one was obtained.

EXAMPLE 33

17α-(2'-methyl-prop-2'-enyl)-17β-hydroxy-9β,10α-androst-4-en-3-one is prepared from 17α-(2'-methyl-prop-2'-enyl)-17β-hydroxy-9β,10β-desA-androstan-5-one by condensation of the latter with methyl vinyl ketone according to the procedure of Example 5. The product melts at 106°–108°.

EXAMPLE 34

16α-Acetoxy-20-ethylenedioxy-pregn-4-en-3-one is prepared by acetylation of 16α-hydroxy 20-ethylenedioxy-pregn-4-ene-3,20-dione with one equivalent of acetic anhydride in pyridine solution at room temperature for 2 hours, followed by concentration to dryness in vacuo. 16α-Acetoxy-20-ethylenedioxy-5-oxo-3,5-seco-A-norpregnan-3-oic acid is prepared by ozonolysis of 16α-acetoxy-20-ethylenedioxy-pregn-4-en-3-one according to the procedure of Example 1.

EXAMPLE 35

16α-Acetoxy-20-ethylenedioxy-10α-desA-pregnan-5-one and 16α-acetoxy-20-ethylenedioxy-10β-desA-pregnan-5-one are prepared from 16α-acetoxy-20-ethylenedioxy-5-oxo-3,5-seco-A-norpregnan-3-oic acid by conversion of the latter to its sodium salt followed by pyrolysis (according to the procedure of Example 2) and reacetylation with acetic anhydride and pyridine.

EXAMPLE 36

16α-Acetoxy-20-ethylenedioxy-desA-pregn-9-en-5-one is prepared from 16α-acetoxy-20-ethylenedioxy-10α-desA-pregnan-5-one by bromination followed by dehydrobromination, according to the procedure of Example 3.

EXAMPLE 37

16α-Acetoxy-20-ethylenedioxy-9β,10β-desA-pregnan-5-one is prepared from 16α-acetoxy-20-ethylenedioxy-desA-pregn-9-en-5-one by hydrogenation under basic conditions in the presence of a rhodium catalyst, according to the procedure of Example 14.

EXAMPLE 38

16α-Hydroxy-20-ethylenedioxy-9β,10α-pregn-4-en-3-one is prepared by condensing 16α-acetoxy-20-ethylenedioxy-desA-9β,10β-pregnan-5-one with methyl vinyl ketone according to the procedure of Example 5.

EXAMPLE 39

3β-Hydroxy-16α-methyl-pregn-5-en-20-one ethylene ketal is prepared by ketalization of 3β-hydroxy-16α-methyl-pregn-5-en-20-one in benzene solution with ethylene glycol using p-toluenesulfonic acid as catalyst. Pyridine-chromic acid oxidation of the so-obtained 3β-hydroxy-16α-methyl-pregn-5-en-20-one ethylene ketal yields 16α-methyl-20-ethylenedioxy-pregn-4-en-3-one. 16α-methyl-20-ethylenedioxy-5-oxo-3,5-seco-A-norpregnane-3-oic acid is prepared by ozonolysis of 16α-methyl-20-ethylene-dioxy-pregn-4-en-3-one according to the procedure of Example 1.

EXAMPLE 40

16α-Methyl-20-ethylenedioxy-10α-desA-pregnan-5-one and 16α-methyl-20-ethylenedioxy-10β-desA-pregnan-5-one are prepared from 16α-methyl-20-ethylenedioxy-5-oxo-3,5-seco-A-norpregnan-3-oic acid by conversion of the latter to its sodium salt followed by pyrolysis, according to the procedure of Example 2.

EXAMPLE 41

16α-Methyl-20-ethylenedioxy-desA-pregn-9-en-5-one is prepared from 16α-methyl-20-ethylenedioxy-10α-desA-pregnan-5-one by bromination followed by dehydrobromination, according to the procedure of Example 3.

EXAMPLE 42

16α-Methyl-20-ethylenedioxy-9β,10β-desA-pregnan-5-one is prepared from 16α-methyl-20-ethylenedioxy-desA-pregn-9-en-5-one by hydrogenation under basic conditions in the presence of a rhodium catalyst, according to the procedure of Example 14.

EXAMPLE 43

16α-Methyl-20-ethylenedioxy-9β,10α-pregn-4-en-3-one is prepared by condensing 16α-methyl-20-ethylenedioxy-9β,10β-desA-pregnan-5-one with methyl vinyl ketone, according to the procedure of Example 5.

EXAMPLE 44

21-Acetoxy-11α-hydroxy-20-ethylenedioxy-pregn-4-en-3-one is prepared by microbiological treatment of 21-acetoxy-20-ethylenedioxy-pregn-4-en-3-one, according to the procedure of Example 17. 21-Acetoxy-11α-mesoxy-20-ethylenedioxy-pregn-4-en-3-one is prepared by treatment of 21-acetoxy-11α-hydroxy-20-ethylenedioxy-pregn-4-ene-3-one with methanesulfonyl chloride, according to the procedure of Example 10.

EXAMPLE 45

21-Acetoxy-11α-mesoxy-20-ethylenedioxy-5-oxo-3,5-seco-A-norpregnan-3-oic acid is prepared by ozonolysis of 21-acetoxy-11α-mesoxy-20-ethylenedioxy-pregn-4-en-3-one, according to the procedure of Example 11.

EXAMPLE 46

21-Acetoxy-20-ethylenedioxy-desA-pregn-9-en-5-one is prepared from 21-acetoxy-20-ethylenedioxy-11α-mesoxy-3,5-seco-A-norpregnan-3-oic acid by conversion of the latter to its sodium salt followed by pyrolysis, according to the procedure of Example 12, except that the crude product is reacetylated by treatment with acetic anhydride/pyridine prior to its being worked-up.

EXAMPLE 47

21-Acetoxy-20-ethylenedioxy-9β,10β-desA-pregnan-5-one is prepared from 21-acetoxy-20-ethylenedioxy-desA-pregn-9-en-5-one by hydrogenation under acidic conditions in the presence of a rhodium catalyst, according to the procedure of Example 15.

EXAMPLE 48

21-Hydroxy-20-ethylenedioxy-9β,10α-pregn-4-en-3-one is prepared from 21-acetoxy-20-ethylenedioxy-9β,10β-desA-pregnan-5-one by condensing the latter with methyl vinyl ketone, according to the procedure of Example 22.

EXAMPLE 49

11α-Mesoxy-16α,17α-isopropylidenedioxy-progesterone is prepared by treatment of 11α-hydroxy-16α,17α-isopropylidenedioxy-progesterone with methane sulfonyl chloride, according to the procedure of Example 10.

EXAMPLE 50

5,20-dioxo-11α-mesoxy-16α,17α-isopropylidenedioxy-3,5-seco-A-norpregnan-3-oic acid is prepared by ozonolysis of 11α-mesoxy-16α,17α-isopropylidenedioxy-progesterone, according to the procedure of Example 11.

EXAMPLE 51

16α,17α-isopropylidenedioxy-desA-pregn-9-en-5,20-dione is prepared from 5,20-dioxo-11α-mesoxy-16α,17α-isopropylidenedioxy-3,5-seco-A-norpregnan-3-oic acid by conversion of the latter to its sodium salt, followed by pyrolysis according to the procedure of Example 12.

EXAMPLE 52

20β-Hydroxy-16α,17α-isopropylidenedioxy-desA-pregn-9-en-5-one is prepared from 16α,17α-isopropylidenedioxy-desA-pregn-9-en-5,20-dione by reduction and reoxidation, according to the procedure of Example 13.

EXAMPLE 53

20β-Hydroxy-16α,17α-isopropylidenedioxy-9β,10β-desA-pregnan-5-one is prepared from 20β-hydroxy-16α,17α-isopropylidenedioxy-desA-pregn-9-en-5-one by hydrogenation according to the procedure of Example 14.

EXAMPLE 54

20β-Hydroxy-16α,17α-isopropylidenedioxy-9β,10α-pregn-4-en-3-one is prepared by condensing methyl vinyl ketone with 20β-hydroxy-16α,17α-isopropylidenedioxy-desA-9β,10β-pregnan-5-one according to the procedure of Example 5.

EXAMPLE 55

7α,17α-dimethyl-17β-hydroxy-5-oxo-3,5-seco-A-norandrostan-3-oic acid is prepared from 7α,17α-dimethyl-testosterone by ozonolysis of the latter, according to the procedure of Example 1.

EXAMPLE 56

7α,17α-dimethyl-17β-hydroxy-10α-desA-androstan-5-one and 7α,17α-dimethyl 17β-hydroxy-10β-desA-androstan-5-one are prepared from 7α,17α-dimethyl-17β-hydroxy-5-oxo-3,5-seco-A-norandrostan-3-oic acid by conversion of the latter to its sodium salt followed by pyrolysis, according to the procedure of Example 2.

EXAMPLE 57

7α,17α-dimethyl-17β-hydroxy-desA-androst-9-en-5-one is prepared from 7α,17α-dimethyl-17β-hydroxy-10α-desA-androstan-5-one by bromination followed by dehydrobromination, according to the procedure of Example 3.

EXAMPLE 58

7α,17α-dimethyl-17β-hydroxy-desA-9β,10β-androstan-5-one is prepared from 7α,17α-dimethyl-17β-hydroxy-desA-androst-9-en-5-one by hydrogenation in the presence of a rhodium catalyst, according to the procedure of Example 4.

EXAMPLE 59

7α,17α-dimethyl-9β,10α-testosterone is prepared from 7α,17α-dimethyl-17β-hydroxy-desA-9β,10β-androstan-5-one by condensing the latter with methyl vinyl ketone, according to the procedure of Example 5.

EXAMPLE 60

11α-Mesoxy-17α-methyl-progesterone is prepared from 11α-hydroxy-17α-methyl-progesterone by treatment of the latter with methane sulfonyl chloride, according to the procedure of Example 10.

EXAMPLE 61

11α-mesoxy-17α-methyl-5,20-dioxo-3,5-seco-A-norpregnan-3-oic acid is prepared from 11α-mesoxy-17α-methyl-progesterone by ozonolysis of the latter, according to the procedure of Example 11.

EXAMPLE 62

17α-methyl-desA-pregn-9-ene-5,20-dione is prepared from 11α-mesoxy-17α-methyl-5,20-dioxo-3,5-seco-A-norpregnan-3-oic acid by conversion of the latter to its sodium salt followed by pyrolysis, according to the procedure of Example 12.

EXAMPLE 63

20β-Hydroxy-17α-methyl-desA-pregn-9-en-5-one is prepared from 17α-methyl-desA-pregn-9-en-5,20-dione according to the procedure of Example 13.

EXAMPLE 64

20β-Hydroxy-17α-methyl-9β,10β-desA-pregnan-5-one is prepared from 17α-methyl-20β-hydroxy-desA-pregnan-9-ene-5-one according to the procedure of Example 15.

EXAMPLE 65

20β-Hydroxy-17α-methyl-9β,10α-pregn-4-en-3-one is prepared by condensing 17α-methyl-20β-hydroxy-9β,10β-desA-pregnan-5-one with methyl vinyl ketone, according to the procedure of Example 4.

EXAMPLE 66

A solution of 12.8 g. of 17α-methyltestosterone in 200 ml. of methylene chloride and 100 ml. of ethyl acetate was ozonized for 1 hour and 5 minutes at −70° (acetone-dry ice bath) until a blue color developed. After oxygen was bubbled through, the solution was then concentrated at room temperature in vacuo. The residue was dissolved in 400 ml. of acetic acid, and after addition of 30 ml. of 30% hydrogen peroxide, the solution was left overnight at 0°. It was then evaporated to dryness in vacuo, the residue taken up in ether, and the ether solution extracted with 2N aqueous sodium carbonate (12 × 50 ml.). The combined carbonate extracts were cooled in ice, and acidified with concentrated hydrochloric acid. The aqueous suspension of precipitated organic acid was extracted with methylene chloride, this extract was washed with water, dried over anhydrous sodium sulfate and evaporated giving as a colorless crystalline material 17β-hydroxy-17α-methyl-5-oxo-3,5-seco-A-nor-androstan-3-oic acid. After recrystallization from acetone-hexane, it melted at 195°–197°, $[\alpha]_D^{25} = 9.8°$ (c = 1.0 in chloroform).

EXAMPLE 67

A solution of 10 g. of 17β-hydroxy-17α-methyl-5-oxo-3,5-seco-A-nor-androstan-3-oic acid in 250 ml. of methanol was made alkaline to phenolphthalein with sodium ethoxide, and evaporated to dryness. The residual powdery sodium salt was mixed well with 32 g. of sodium phenylacetate and 40 g. of neutral alumina (Woelm, Grade I), and the mixture heated at 290° in vacuo for 4 hours. After cooling to room temperature, a large excess of water was added, and the resultant suspension extracted with 2 liters of ether. The ether extract was washed with water, aqueous 2N sodium carbonate solution, and again with water, dried and evaporated. This gave a sirupy residue, which by thin layer chromatograms and infrared spectra consisted of 17β-hydroxy-17α-methyl-10α-desA-androstan-5-one as the major and 17β-hydroxy-17α-methyl-10β-desA-androstan-5-one as the minor product.

Three additional pyrolyses were performed as described above, and the combined products so-obtained was chromatographed on a 850 g. silica gel column, using 5% ethylacetate in benzene as the eluent. This chromatography yielded 17β-hydroxy-17α-methyl- 10α-desA-androstan-5-one, which after recrystallization from petroleum ether melted at 96°–97°, $[\alpha]_D^{25} = 28.2°$ (c = 0.5 in chloroform).

Further eluates of the column gave product, 17β-hydroxy-17α-methyl-10β-desA-androstan-5-one which, when recrystallized from ether, melted at 165°–167°, $[\alpha]_D^{25} = -19.8°$ (c = 0.5 in chloroform).

To a solution of 2.2 g. of the mixture of 17β-hydroxy-17α-methyl-10α-desA-androstan-5-one and 17β-hydroxy-17α-methyl-10β-desA-androstan-5-one (obtained by the above pyrolysis procedure) in 50 ml. of absolute ethanol were added 20.1 ml. of a solution prepared by dissolving 2.48 g. of sodium metal in 250 ml. of absolute ethanol. The reaction mixture was stirred overnight at room temperature. It was then acidified with 2 ml. of glacial acetic acid, and evaporated to dryness. The residue was extracted in ether (1 liter) and the ether extract washed with water, dried, and evaporated. The residue was crystallized from petroleum ether giving a quantitative yield of 17β-hydroxy-17α-methyl-10α-desA-androstan-5-one.

EXAMPLE 68

To a solution of 11.2 g. of 17β-hydroxy-17α-methyl-10α-desA-androstan-5-one in 1260 ml. of anhydrous ether, stirred and cooled in an ice-salt bath, were added first several drops of 30% hydrogen bromide in acetic acid, then dropwise a solution of 7.16 g. of bromine in 20 ml. of glacial acetic acid. The rate of addition of the bromine solution was synchronized with the rate of disappearance of excess bromine. After bromination was complete, 53 ml. of 10% sodium hydrogen sulfite solution and 53 ml. of aqueous 2N sodium carbonate solution were added to the reaction mixture while stirring. The ether layer was then separated, washed with water, dried, and evaporated to dryness in vacuo. The residue was dissolved in 250 ml. of dimethylformamide, and heated with 7.5 g. of lithium carbonate at 100° for 45 minutes. After cooling, 2 liters of ether were added and the ether solution washed with water, 1N hydrochloric acid, and then again with water, dried and evaporated. The residue was dissolved in 200 ml. of glacial acetic acid, 12.6 g. of sodium acetate and 12.6 g of zinc powder were added and the mixture heated for ten minutes at 80°. After cooling to room temperature, the reaction mixture was filtered, and evaporated. The residue was dissolved in ethylacetate, and washed with saturated sodium bicarbonate solution, then with water, dried and evaporated. The so-obtained residue was chromatographed on a silica gel column using 10% ethylacetate in benzene as the eluent which gave first 17β-hydroxy-17α-methyl-10α-desA-androstan-5-one, followed by 17β-hydroxy-17α-methyl-desA-androst-9-en-5-one. After recrystallization from ether, the latter compound melted at 103°–104°, $[\alpha]_D^{25} = -63.2°$ (c = 0.5 in chloroform).

EXAMPLE 69

A suspension of 1.25 g. of 5% rhodium on alumina catalyst in a mixture of 130 ml. of 95% ethanol and 26 ml. of 2N sodium hydroxide was prereduced. To this was then added a solution of 1.25 g. of 17β-hydroxy-17α-methyl-desA-androst-9-en-5-one in 75 ml. of 95% ethanol, and then the mixture was hydrogenated at atmospheric pressure and room temperature. After one mole equivalent of hydrogen was absorbed, the reaction was stopped, the catalyst was removed by filtration, and the filtrate evaporated in vacuo. To the residue 5 ml. of glacial acetic acid was added, the so-formed mixture then dissolved in 2 liters of ether, and the resultant cloudy solution was washed with water, then dried and evaporated. The residue was dissolved in 50 ml. of methylene chloride and oxidized with 5 ml. of 2% chromic acid in 90% acetic acid until green color of reaction mixture. After then being washed with sodium hydrogen sulfite solution 2N sodium carbonate solution and water, the reaction mixture was dried over sodium sulfate and evaporated. The residue was chromatographed very slowly on a 50 g. silica gel column, with 5% ethylacetate in benzene, and followed with thin layer chromatography. First, 17β-hydroxy-17α-methyl-9α,10α-desA-androstan-5-one was eluted. After a minor amount of mixed material, 17β-hydroxy-17α-methyl-9β,10β-desA-androstan-5-one was eluted. After recrystallization from ether-petroleum ether, it melted at 94°–96°.

EXAMPLE 70

17α-Methyl-9β,10α-testosterone is prepared from 17α-methyl-17β-hydroxy-desA-9β,10β-androstan-5-one by condensation of the latter with methyl vinyl ketone, according to the procedure of Example 5. The product melts at 128°–129°.

EXAMPLE 71

A solution of 6 g. of 11α,20β-diacetoxy-pregn-4-en-3-one in 100 ml. methylene chloride and 50 ml. of ethylacetate was ozonized at −70°. After methylene chloride was removed by distillation in vacuo, the residual solution was diluted to 100 ml. with ethylacetate. To this 5 ml. of 30 per cent hydrogen peroxide was added and left overnight at room temperature. The reaction mixture was concentrated to dryness in vacuo, the residue taken up in 1 liter of ether, and the resulting solution extracted 10 times with 50 ml. portions of 2N aqueous sodium carbonate. The carbonate extract was then acidified with ice-cold concentrated hydrochloric acid. The precipitated product was separated by filtration, and crystallized to give 11α,20β-diacetoxy-5-oxo-3,5-seco-A-nor-pregnan-3-oic acid.

EXAMPLE 72

A methanolic solution of 5 g. of 11α,20β-diacetoxy-5-oxo-3,5-seco-A-nor-pregnan-3-oic acid was treated with one-half mole equivalent of sodium carbonate, and evaporated to dryness in vacuo. Potassium acetate (5 g.) was added to the residue which was then pyrolyzed at 295° and 0.02 mm. The sublimate was chromatographed on a silica-gel column to give 11α,20β-diacetoxy-10β-desA-pregnan-5-one.

EXAMPLE 73

Bromination and dehydrobromination starting with 11α,20β-diacetoxy-10β-desA-pregnan-5-one according to the procedure of Example 3, gave 11α,20β-diacetoxy-desA-pregn-9-en-5-one.

EXAMPLE 74

Hydrogenation of 11α,20β-diacetoxy-desA-pregn-9-en-5-one in ethanolic hydrochloric acid over 5 per cent rhodium on alumina catalyst at room temperature and atmospheric pressure according to the procedure of Example 15 gave 11α,20β-diacetoxy-9β,10β-desA-pregnan-5-one.

EXAMPLE 75

11α,20β-Diacetoxy-9β,10β-desA-pregnan-5-one was hydrolyzed in methanol solution with one mole equivalent of potassium carbonate to give 11α,20β-dihydroxy-9β,10β-desA-pregnan-5-one.

EXAMPLE 76

Condensation of 11α,20β-dihydroxy-9β,10β-desA-pregnan-5-one with methyl vinyl ketone according to the procedure of Example 5 gave 11α,20β-dihydroxy-9β,10α-pregn-4-en-3-one.

EXAMPLE 77

A solution of 3 g. of 17α-ethyl-17β-hydroxy-androsta-1,4-dien-3-one in 75 ml. of methylene chloride and 25 ml. of ethyl acetate was ozonized at −70° till it became blue. After evaporation to dryness, the residue was dissolved in 100 ml. of glacial acetic acid containing 5 ml. of 30 per cent hydrogen peroxide, and set at room temperature for 2 days. The reaction mixture was concentrated to dryness and the residue dissolved in one liter of ether. The ether solution was then extracted 10 times with 25 ml. portions of aqueous 2N sodium carbonate solution, and the carbonate extracts were acidified with ice-cold concentrated hydrochloric acid. The non-crystalline precipitate containing 17α-ethyl-17β-hydroxy-10α-carboxy-desA-androstan-5-one was separated by filtration and dried, then dissolved in 135 ml. of absolute ethanol, and after addition of 9 ml. of aqueous 2N sodium hydroxide, boiled for 1 hr. The reaction mixture was concentrated in vacuo to a small volume, and diluted with 1750 ml. of ether. The ether solution was washed with water, dried over anhydrous sodium sulfate, and concentrated in vacuo to dryness. The residue was crystallized from ether-petroleum ether, to give 17α-ethyl-17β-hydroxy-10α-desA-androstan-5-one, m.p. 89°–90°.

EXAMPLE 78

3-(17β-hydroxy-5-oxo-3,5-seco-A-nor-androstan-17α-yl-3-oic acid)-propionic acid lactone is prepared by ozonolysis of 3-(3-oxo-17β-hydroxy-androst-4-en-17α-yl)-propionic acid lactone, according to the procedure of Example 1.

EXAMPLE 79

3-(17β-hydroxy-5-oxo-10α-desA-androstan-17α-yl)-propionic acid lactone and 3-(17β-hydroxy-5-oxo-10β-desA-androstan-17α-yl)-propionic acid lactone are prepared from 3-(17β-hydroxy-5-oxo-3,5-seco-A-nor-androstan-17α-yl-3-oic acid)-propionic acid lactone by conversion of the latter to its sodium salt followed by pyrolysis, according to the procedure of Example 2.

EXAMPLE 80

3-(17β-hydroxy-5-oxo-desA-androst-9-en-17α-yl)-propionic acid lactone is prepared from 3-(17β-hydroxy-5-oxo-10α-desA-androstan-17α-yl)-propionic acid lactone by bromination followed by dehydrobromination, according to the procedure of Example 3.

EXAMPLE 81

3-(17β-hydroxy-5-oxo-9β,10β-desA-androstan-17α-yl)-propionic acid lactone is prepared from 3-(17β-hydroxy-5-oxo-desA-androst-9-en-17α-yl)-propionic acid lactone by hydrogenation in the presence of a rhodium catalyst, according to the procedure of Example 4.

EXAMPLE 82

3-(17β-hydroxy-3-oxo-9β,10α-androst-4-en-17α-yl)-propionic acid lactone is prepared by condensing 3-(17β-hydroxy-5-oxo-9β,10β-desA-androstan-17α-yl)-propionic acid lactone with methyl vinyl ketone, according to the procedure of Example 5.

EXAMPLE 83

17α,20;20,21-bis-methylenedioxy-11α-mesyloxy-pregn-4-en-3-one is prepared by treatment of 17α,20;20,21-bis-methylenedioxy-11α-hydroxy-pregn-4-en-3-one with methanesulfonyl chloride according to the procedure of Example 10.

EXAMPLE 84

17α,20;20,21-bis-methylenedioxy-11α-mesyloxy-5-oxo-3,5-seco-A-norpregnan-3-oic acid is prepared by ozonolysis of 17α,20;20,21-bis-methylenedioxy-11α-mesyloxy-pregn-4-en-3-one according to the procedure of Example 11.

EXAMPLE 85

17α,20;20,21-bis-methylenedioxy-desA-pregn-9-en-5-one is prepared from 17α,20;20,21-bis-methylenedioxy-11α-mesyloxy-5-oxo-3,5-seco-A-norpregnan-3-oic acid by conversion of the latter to its sodium salt followed by pyrolysis, according to the procedure of Example 12.

EXAMPLE 86

17α,20;20,21-bis-methylenedioxy-9β,10β-desA-pregnan-5-one is prepared from 17α,20;20,21-bis-methylenedioxy-desA-pregn-9-en-5-one by hydrogenation in the presence of a rhodium catalyst according to the procedure of Example 14.

EXAMPLE 87

17α,20;20,21-bis-methylenedioxy-9β,10α-pregn-4-en-3-one is prepared by condensing methylvinyl ketone with 17α,20;20,21-bis-methylenedioxy-9β,10β-desA-pregnan-5-one, according to the procedure of Example 5.

EXAMPLE 88

20β-hydroxy-9β,10α-pregna-1,4-dien-3-one was prepared by condensation of 20β-hydroxy-9β,10β-desA-pregnan-5-one with 1 equivalent of methyl ethinyl ketone in boiling benzene solution, catalyzed by sodium hydride.

EXAMPLE 89

One ml. of Jones Reagent (0.004 mole $CrO_3$) is added to 200 mg. of 17β-hydroxy-9β,10β-desA-androstan-5-one in 20 ml. of acetone at −10°. The mixture is then left for 15 minutes at room temperature, and 5 ml. of ethanol then added. The resulting suspension is evaporated to dryness in vacuo, water is added to the residue and the undissolved moiety taken up in ether. The ether phase is then washed with a solution of sodium bicarbonate and then with water, dried over sodium sulfate and evaporated to dryness. There is so obtained an oil which crystallizes upon the addition of a small portion of petroleum ether. The so-obtained crystals of 9β, 10β-desA-androstane-5,17-dione melt, after recrystallization from cyclohexane, at 77.5°–78°; $[\alpha]_{589}^{25}$ +55°(c = 0.107, dioxane); R.D. in dioxane (c = 0.107%): λ in mμ ([α]-value in °); 550(+70); 400(+297); 350(+798); 320(+2968) max.; 300(+467); 299(0); 290(−1890).

EXAMPLE 90

A solution of 250 mg. of 17β-hydroxy-9β,10β-desA-androstan-5-one dissolved in 2.5 ml. of pyridine and 2.5 ml. of acetic anhydride, is left at room temperature for 18 hours. The mixture is then evaporated to dryness at 80°/11 mm., the residue taken up in ether, and the ether phase washed with 1N hydrochloric acid, sodium bicarbonate and water, and then dried over sodium sulfate. After filtration and evaporation of the ether, the residue is then treated with a small quantity of petroleum ether yielding crystals of 17β-acetoxy-9β,10β-desA-androstan-5-one which, upon recrystallization from methanol, melt at 118°–119°; $[\alpha]_{589}^{25°} = -28°$ (c = 0.103%, dioxane); R.D. in dioxane (c = 0.103%): λ in mμ ($[\alpha]$-value in °); 400 (−30); 356 (0); 350 (+10); 313 (+449) max.; 307 (+374) min.; 305 (+380) max.; 300 (+224); 293 (0); 280 (−652).

EXAMPLE 91

A solution of 250 mg. of 17β-acetoxy-9β,10β-desA-androstan-5-one in 60 ml. of 95% methanol containing 144 mg. of potassium hydroxide is refluxed for 60 minutes. The resulting mixture is evaporated to dryness in vacuo, water added to the residue and the suspension extracted with ether. The ether phase is washed with water, dried over sodium sulfate, filtered off, the solvent removed and the crystalline residue then crystallized from a small volume of cyclohexane, yielding crystals of 17β-hydroxy-9β,10β-desA-androstan-5-one which upon being recrystallized from ethylacetate melt at 144.5°–145°; $[\alpha]_{589}^{25} = -22°$ (c = 0.103, dioxane), R.D. in dioxane (c = 0.103); λ in mμ ($[\alpha]$-value in °); 400 (−7); 390 (0); 350 (+52); 313 (+571) max.; 307 (+492) min.; 305 (+504) max; 300 (+324); 293 (0); 290 (−202).

EXAMPLE 92

A solution of 10 g. of 11β-formyloxy-androsta-1,4-diene-3,17-dione in 100 ml. of acetic acid was ozonized at 0° until thin layer chromatography did not show any starting material. The reaction mixture was then poured into 100 ml. of water and the mixture was then heated to 100° for 30 minutes. The mixture was then concentrated in vacuo and treated with 50 ml. of saturated sodium bicarbonate solution. The undissolved material was extracted with 100 ml. of ether. The extract was chromatographed on silica gel using methylene chloride. The eluates were concentrated and gave, on addition of hexane, 11β-formyloxy-10ε-desA-androstane-5,17-dione, m.p. 117°–117.5° (recrystallized from acetone-cyclohexane), $[\alpha]_D^{25} = 93°$ (dioxane).

EXAMPLE 93

By hydrolysis of 11β-formyloxy-10ε-desA-androstane-5,17-dione in 2% methanolic potassium hydroxide there is obtained 11β-hydroxy-10ε-desA-androstan-5,17dione, which melts at 154°; $[\alpha]_D^{25} +96°$ (dioxane).

EXAMPLE 94

250 mg. of 11β-hydroxy-10ε-desA-androstane-5,17-dione and 250 mg. of p-toluene sulfonic acid monohydrate in 20 ml. of benzene were refluxed in a nitrogen atomsphere for 6 hours. The reaction mixture was then washed with an aqueous solution of sodium bicarbonate and then with water, dried over sodium sulfate, filtered and evaporated to dryness. The residue was then chromatographed over silicagel (5 g.) in dichloromethane. Triturating the residue obtained from the first 250 ml. eluted, yielded crystals of desA-androst-9-ene-5,17-dione, which upon recrystallization from cyclohexane melted at 123°–123.5°.

EXAMPLE 95

The compound, 11β-formyloxy-5,17-dioxo-3,5-seco-A-norandrostan-3-oic acid is prepared from 11β-formyloxy-androst-4-ene-3,17-dione by ozonolysis according to the procedure of Example 11. The so-obtained product melts at 220°–221°; $[\alpha]_D^{25} +107°$ (dioxane).

EXAMPLE 96

3.7 g. of the sodium salt of 11β-formyloxy-5,17-dioxo-3,5-seco-A-nor-androstan-3-oic acid and 12 g. of sodium phenylacetate are fused together in vacuo (0.1 Torr). When the bath temperature reaches 220° the molten mass begins to decompose. The bath is then heated further (within 30 minutes) to a temperature of 290°. Once this temperature has been reached the mixture is left for another 10 minutes at the initial pressure of 0.1 Torr. The distilled material is then chromatographed over 30 g. of aluminum oxide (activity grade 3). Elution with a total of 200 ml. of petroleum ether-benzene (2:1), followed by evaporation of the solvent and trituration of the residue in the presence of petroleum ether, yields desA-androst-9-ene-5,17-dione which upon recrystallization from cyclohexane melts at 123°–123.5°; $[\alpha]_D^{25} = +83°$ (c = 0.1021, dioxane).

EXAMPLE 97

20β-Acetoxy-5-oxo-3,5-seco-A-nor-pregnan-3-oic acid is prepared by ozonolysis of 20β-acetoxy-pregn-4-en-3-one according to the procedure of Example 1.

EXAMPLE 98

A solution of 15.15 g. of 20β-acetoxy-5-oxo-3,5-seco-A-nor-pregnan-3-oic acid in 250 ml. of 75% methanol containing 10 g. of potassium hydroxide was refluxed for 2 hours. The methanol was then removed in vacuo and the residue was dissolved in 100 ml. of water. The solution was chilled to 0° and acidified to congo red by the addition of 20% hydrochloric acid. There was thus obtained 20β-hydroxy-5-oxo-3,5-seco-A-nor-pregnan-3-oic acid, m.p. 181°–182°,$[\alpha]_D^{25} = 13°$ (dioxane).

A solution of 4.7 g of 20β-hydroxy-5-oxo-3,5-seco-A-nor-pregnan-3-oic acid in 100 ml. of methanol was neutralized with 1N sodium methylate solution against phenolphthaleine. The solution was then evaporated and the residue, consisting of 20β-hydroxy-5-oxo-3,5-seco-A-nor-pregnan-3-oic acid sodium salt, was refluxed with 100 ml. of quinoline for 8 hours. The cooled mixture was poured on a mixture of 150 g. of ice and 100 ml. concentrated hydrochloric acid and extracted with ether. The ether extract was worked up and the oily residue was chromatographed on silica gel. Elution with methylene chloride gave 10α-desA-pregnane-5,20-dione, m.p. 126°–127° (crystallized from isopropyl ether), $[\alpha]_D^{25} = 82°$ (dioxane). Elution with methylene chloride containing 1% acetone gave 20β-hydroxy-10α-desA-pregnan-5-one, m.p. 104°–104.5° (crystallized from ether-hexane), $[\alpha]_D^{25} = -10°$ (dioxane). The fractions obtained with methylene chloride containing 5–10% acetone were evaporated and the oily residue was dissolved in 40 ml. of acetone. The solution was treated with 3 ml. of Jones reagent (0.004 mole CrO₃) at −10° and kept at the same temperature for 10 minutes. After the addition of 5 ml. of methanol, the solution was evaporated and the residue was diluted with water and extracted with ether. The ether extract was worked up and gave 10α-desA-pregnane-5,20-dione.

EXAMPLE 99

20β-hydroxy-desA-pregn-9-en-5-one is prepared from 20β-hydroxy-10α-desA-pregnan-5-one by bromination followed by dehydrobromination, according to the procedure of Example 3. The so-obtained product, after recrystallization from methylene chloride-petroleum ether, melts at 122°-123°.

EXAMPLE 100

5,20-dioxo-3,5-seco-A-nor-pregnan-3-oic acid is prepared by ozonolysis of progesterone according to the procedure of Example 1.

EXAMPLE 101

10α-desA-pregna-5,20-dione and 10β-desA-pregnan-5,20-dione are prepared from 5,20-dioxo-3,5-seco-A-nor-pregnan-3-oic acid by conversion of the latter to its sodium salt followed by pyrolysis, according to the procedure of Example 2.

EXAMPLE 102

The compound, desA-pregn-9-ene-5,20-dione is prepared from 10α-desA-pregna-5,20-dione by bromination followed by dehydrobromination according to the procedure of Example 3. The so-obtained product, after recrystallization from ether, melts at 111°-113°.

EXAMPLE 103

15 ml. of 0.8% potassium permanganate solution was added to a mixture of 11 g. of 20β tetrahydropyranyloxy-pregn-4-en-3-one, 500 ml. of an azeotropic mixture of tertiary butanol and water, 7 g. of potassium carbonate, 20 ml. of water and 120 ml. of 7% sodium metaperiodate solution with vigorous stirring at room temperature. 250 ml. of 7% sodium metaperiodate and 20 ml. of 0.8% potassium permanganate solution were then simultaneously added within 15 minutes. To the so-obtained suspension, 220 ml. of 7% sodium metaperiodate solution and, in order to keep the mixture violet in color, 15 ml. of 0.8% potassium permanganate solution were then added in the course of 30 minutes. The mixture was then stirred for 90 minutes, filtered over a filter aid (Hyflo) and the residue was washed with 100 ml. of tert. butanol-water azeotrope. The filtrate was evaporated in vacuo at 50° and the residue diluted with 150 ml. of water. The solution was acidified with cold 20% hydrochloric acid to congo red, and the resultant oily material taken up in 150 ml. of methylene chloride. The organic extract was washed with water, dried and evaporated and the residue was purified by filtration over silica gel using methylene chloride and methylene chloride containing 1-2% ethanol as the elution agents. There was thus obtained 20β-tetrahydropyranyloxy-5-oxo-3,5-seco-A-nor-pregnan-3-oic acid as a viscous oil.

EXAMPLE 104

To a solution of 35.8 g. of a mixture of 20α- and 20β-hydroxy-pregn-4-en-3-one in 500 ml. of anhydrous benzene, there were added 75 ml. of 1% p-toluenesulfoniic acid in benzene and then 35 ml. of dihydropyan. The reaction mixture was allowed to stand at room temperature for 16 hours, washed with 2% aqueous sodium bicarbonate and water, dried and concentrated in vacuo at 11 mm. Hg and 80°. The residue consisting of 20α- and 20β-tetrahydropyranyloxy-pregn-4-en-3-one was dissolved in 2 liters of tert. butanol-water azeotrope followed by the addition of a solution of 33 g. of potassium carbonate in 80 ml. of water and 620 ml. of 7% aqueous sodium metaperiodate solution. To the reaction mixture there was first added with vigorous stirring at room temperature, 75 ml. of 0.8% potassium permanganate and thereafter simultaneously within 30 minutes 1350 ml. of 7 % sodium metaperiodate solution and 100 ml. of 0.8% potassium permangante solution. Another 1080 ml. of 7% sodium metaperiodate solution and 100 ml. of 0.8% potassium permangante solution were then added within 45 minutes. The reaction mixture was then stirred for 1 hour, filtered over a filter aid (Hyflo) and the residue was washed with 250 ml. of tert. butanol-water azeotrope. The filtrate was evaporated, the residue taken up in 800 ml. of water and filtered. The alkaline filtrate was chilled to 0°, acidified with cold 20% hydrochloric acid and extracted with methylene chloride. After working up, the extract afforded a mixture of 20α- and 20β-tetrahydropyranyloxy-5-oxo-3,5-seco-A-nor-pregnan-3-oic acid as a viscous oil. This oil was dissolved in 300 ml. of methanol and neutralized with 1N lithium methylate. The solution was evaporated to dryness in vacuo. The oily residue was dissolved in 300 ml. of benzene, evaporated again and dried at 11 mm. Hg and 100° for 2 hours. There was obtained a mixture of the lithium salts of 20α- and 20β-tetrahydropyranyloxy-5-oxo-3,5-seco-A-nor-pregnan-3-oic acid as an amorphous powder.

EXAMPLE 105

A solution of 9 g. of 20β-tetrahydropyranyloxy-5-oxo-3,5-seco-A-nor-pregnan-3-oic acid in 100 ml. of methanol was neutralized with 1N lithium methylate solution against phenolphthaleine, followed by evaporation in vacuo to dryness. The so-obtained residue was taken up in benzene, and the benzene evaporated yielding 20β-tetrahydropyranyloxy-5-oxo-3,5-seco-A-nor-pregnan-3-oic acid lithium salt as a semi-crystalline powder.

5 g. of this lithium salt, 7.5 g. of anhydrous sodium acetate and 7.5 g. of anhydrous potassium acetate were mixed and pyrolyzed at 0.02-0.1 mm. Hg and 290° for 4 hours. The distillate was chromatographed on silica gel using methylene chloride and methylene chloride containing 0.5-1% acetone as the elution agents. The fractions were evaporated and gave on treatment with etherhexane 20β-tetrahydropyranyloxy-10α-desA-pregnan-5-one, m.p. 125.5°-127° (crystallized from methanol) $[\alpha]_D^{25} = 53°$ (dioxane).

The oily part of the evaporation residue containing besides the latter compound the compound 20β-tetrahydropyranyloxy-10β-desA-pregnan-5-one ethanol. After the addition of 10 ml. of water and 200 mg. of p-toluenesulfonic acid monohydrate, the solution was refluxed for 60 minutes and evaporated in vacuo. The residue was then treated with water and extracted with ether. The ether extract was worked up and gave 20β-hydroxy-10α-desA-pregnan-5-one, m.p. 104.5°-105° (crystallized from ether-hexane).

EXAMPLE 106

250 mg. of 20β-tetrahydropyranyloxy-10α-desA-pregnan-5-one was dissolved in 8 ml. of ethanol and after the addition of 1 ml. of water and 15 mg. of p-toluenesulfonic acid monohydrate refluxed for 1 hour. The reaction mixture was then evaporated and the residue taken up in ether. The ether extract was worked up and gave 20β-hydroxy-10α-desA-pregnan-5-one, m.p. 104.5°–105° (crystallized from ether-hexane).

EXAMPLE 107

10 g. of a mixture of 20α- and 20β-tetrahydropyranyloxy-5-oxo-3,5-seco-A-nor-pregnan-3-oic acid lithium salt was mixed with 15 g. each of anhydrous sodium acetate and anhydrous potassium acetate and pyrolyzed at 0.01–0.1 mm. Hg and 290° for 5 hours. The distillate was dissolved in 100 ml. of ethanol and, after the addition of 15 ml. of water and 250 mg. of p-toluenesulfonic acid monohydrate refluxed for 70 minutes. The reaction mixture was then evaporated, the residue was treated with 50 ml. of 5% sodium bicarbonate solution and extracted with ether. On working up, the extract gave an oily residue of 20α- and 20β-hydroxy-10α-desA-pregnan-5-one, which was dissolved in 80 ml. of acetone, treated with 10 ml. of Jones reagent at −10° and kept at −10° for 15 minutes. The suspension obtained was treated with 15 ml. of ethanol, kept for 10 minutes at room temperature and evaporated. The residue was diluted with water and extracted with ether. The extract was worked up and gave, on addition of hexane, 10α-desA-pregnane-5,20-dione, m.p. 126°–127° (crystallized from isopropyl ether). The above pyrolysis was carried out in the same manner using 10 g. of the lithium salt mixture and 30 g. of sodium phenylacetate.

EXAMPLE 108

40 ml. of 0.8% potassium permanganate solution was added with vigorous stirring to a mixture prepared from 25 g. of testosterone acetate, 1000 ml. of tert. butanol-water azeotrope, 16.8 g. of potassium carbonate and 300 ml. of 7% aqueous sodium metaperiodate solution. In the course of 15 minutes, 660 ml. of 7% sodium metaperiodate solution and 40 ml. of 0.8% potassium permanganate solution were then simultaneously added to the so-formed reaction mixture, followed by the addition of 540 ml. of 7% sodium metaperiodate solution and 20 ml. of 0.8% potassium permanganate solution in the course of 30 minutes. The mixture was then stirred for 90 minutes, filtered over a filter aid (Hyflo) and the residue was washed with 150 ml. of tert. butanol-water azeotrope. The filtrate was worked up as described in Example 104 and gave 17β-acetoxy-5-oxo-3,5-seco-A-nor-androstan-3-oic acid, a viscous oil. This oil was dissolved in 250 ml. of methanol, the solution was mixed with a solution of 15 g. of potassium hydroxide in 100 ml. of water and allowed to stand for 16 hours. The solution was then concentrated in vacuo. The residue was dissolved in 100 ml. of water, acidified with 20% hydrochloric acid and extracted with methylene chloride. The extract was worked up and gave 17β-hydroxy-5-oxo-3,5-seco-A-nor-androstan-3-oic acid, m.p. 202.5°–203° (crystallized from ethanol).

EXAMPLE 109

A solution of 14.2 g. of 17β-hydroxy-5-oxo-3,5-seco-A-nor-androstan-3-oic acid in 280 ml. of anhydrous benzene was allowed to stand with 25 ml. of 1% p-toluenesulfonic acid in benzene and 11 ml. of dihydropyran at room temperature for 1 hour. The reaction mixture was then poured on ice and extracted with ether. The ether extract was washed with sodium hydrogen carbonate solution and water and evaporated. The oily residue consisted of a mixture of 17β-tetrahydropyranyloxy-5-oxo-3,5-seco-A-nor-androstan-3-oic acid and its tetrahydropyranyl ester. The mixture was converted into the free acid by alkaline hydrolysis.

EXAMPLE 110

5 g of 17β-tetrahydropyranyloxy-5-oxo-3,5-seco-A-nor-androstan-3-oic acid lithium salt (prepared by treating the free acid with 1N lithium methylate according to the procedure of Example 105) was pyrolyzed in a mixture of 7.5 g. each of sodium acetate and potassium acetate at 0.05–0.01 mm. Hg and 280°–310° for 80 minutes. The distillate was worked up and the neutral part was chromatographed on silica gel. Using petroleum ether-ether (8:2 to 6:4) there was obtained partly cyrstalline 17β-tetrahydropyranyloxy-10α-desA-androstan-5-one, $[\alpha]_D^{25} = -16°$ (dioxane).

The same product was obtained by pyrolysis of the sodium salt at normal pressure under nitrogen and by pyrolysis of the lithium salt in quinoline at 300° and 4.5 atmospheres. However, better yields were achieved by carrying out the pyrolysis in molten sodium phenylacetate.

EXAMPLE 111

30 ml. of 0.8% potassium permanganate solution was added under vigorous stirring to a solution prepared from 19.8 g. of 11β-formyloxy-androst-4-en-3,17-dione, 600 ml. of tert. butanol-water azeotrope, 12.6 g. of potassium carbonate and 225 ml. of 7% sodium metaperiodate solution. In the course of 15 minutes, 500 ml of 7% sodium metaperiodate solution and 20 ml. of 0.8% potassium permanganate solution were then simultaneously added to the reaction mixture, followed by the addition of another 500 ml. of 7% sodium metaperiodate solution and 15 ml. of 0.8% potassium permanganate solution in the course of 30 minutes. The so-obtained mixture was then stirred for 90 minutes, filtered over a filter aid (Hyflo) and the residue was washed with 60 ml. of tert. butanol-water azeotrope. The filtrate was then worked up as described in Example 104 and gave 11β-formyloxy-5,17-dioxo-3,5-seco-A-nor-androstan-3-oic acid, m.p. 220°–221° (from ethanol), $[\alpha]_D^{25} = 107°$ (dioxane).

The starting 11β-formyloxy-androst-4-ene-3,17-dione was prepared from 11β-hydroxy-androst-4-ene-3,17-dione by dissolving the latter in excess formic acid in the presence of a catalytic amount of perchloric acid and, after 20 hours at room temperature, pouring the reaction mixture on ice, extracting with methylene chloride and evaporating. There was obtained a product melting at 139°–139.5° (crystallized from ethyl acetate), $[\alpha]_D^{25} = 188°$ (dioxane).

EXAMPLE 112

A solution of 10 g. of 11β,17β-diformyloxy-androsta-1,4-dien-3-one in 100 ml. of acetic acid was ozonized at 0° until thin layer chromatography did not show any starting meterial. The solution was then diluted with 100 ml. of water, heated to 100° for 30 minutes and evaporated. The residue was worked up according to the procedure of Example 92, giving 11β,17β-diformyloxy-10ε-desA-androstan-5-one, m.p. 164°–166° (crystallized from methanol), $[\alpha]_D^{25} = 21°$ (chloroform). Further elution using methylene chloride containing 1% acetone gave 11β-formyloxy-17β-hydroxy-10ε-desA-androstan-5-one, m.p. 128°–128.5° (crystallized from isopropyl ether), $[\alpha]_D^{25} = 51°$ (chloroform):

The starting 11β,17β-diformyloxy-androsta-1,4-dien-3-one was prepared from 11β,17β-dihydroxyandrosta-1,4-dien-3-one by a procedure analogous to that of Example 111. The product melts at 253°–254° (crystallized from methanol-methylene chloride), $[\alpha]_D^{25} = 72°$ (dioxane).

EXAMPLE 113

A solution of 800 mg. of 11β-formyloxy-17β-hydroxy-10ε-desA-androstan-5-one in 15 ml. of methanol was mixed with a solution of 600 mg. of potassium hydroxide in 1.5 ml. of water and kept at room temperature for 1 hour. The solution was then treated with 0.5 ml. of acetic acid and evaporated in vacuo to dryness. The residue was taken up in methylene chloride and the extract was worked up. There was obtained 11β,17β-dihydroxy-10ε-desA-androstan-5-one, m.p. 174.5°–175° (crystallized from ethyl acetate-hexane), $[\alpha]_D^{25} = 36°$ (chloroform).

EXAMPLE 114

1500 ml. of 16% aqueous sodium metaperiodate solution and 300 ml. of 0.8% potassium permanganate solution were added in the course of 50 minutes at room temperature to a solution of 25 g. of 17β-tetrahydropyranyloxy-androst-4-en-3-one, 1000 ml. of tert. butanol-water azeotrope, 16.8 g. of potassium carbonate and 40 ml. of water. The reaction mixture was then stirred for another 1.5 hours and filtered through a filter aid (Speedex). The precipitate was then washed with tert. butanol-water azeotrope and worked up as described in Example 104 affording 17β-tetrahydropyranyloxy-5-oxo-3,5-seco-A-nor-androstan-3-oic acid as an oil.

EXAMPLE 115

120 ml. of 2% ethereal diazomethane solution was added in the course of 30 minutes with cooling to a suspension of 10 g of 20β-hydroxy-5-oxo-3,5-seco-A-nor-pregnan-3-oic acid in 100 ml. of methylene chloride. The so-obtained solution was kept at room temperature for 30 minutes and the excess diazomethane was destroyed by the addition of a small amount of acetic acid. The solution was then evaporated and the residue gave, on recrystallization from ethyl acetate, 20β-hydroxy-5-oxo-3,5-seco-A-nor-pregnan-3-oic acid methyl ester, m.p. 110°–111°, $[\alpha]_D^{25} = 16°$ (dioxane).

EXAMPLE 116

15 ml. of 1% p-toluenesulfonic acid in benzene and then 7 ml. of dihydropyran were added to a solution of 10 g. of 20β-hydroxy-5-oxo-3,5-seco-A-nor-pregnan-3-oic acid methyl ester in 130 ml. of anhydrous benzene. The reaction mixture was kept at room temperature for 4 hours and then poured on 50 ml. of ice water. The organic layer was washed with 2% sodium bicarbonate solution and then with water, dried and evaporated in vacuo, yielding 20β-tetrahydropyranyloxy-5-oxo-3,5-seco-A-nor-pregnan-3-oic acid methyl ester as a colorless, viscous oil.

EXAMPLE 117

50 ml. of 20% aqueous potassium hydroxide was added to a solution of 10 g. of 20β-tetrahydropyranyloxy-5-oxo-3,5-seco-A-nor-pregnan-3-oic acid methyl ester in 150 ml. of methanol. The reaction mixture was then refluxed for 70 minutes and evaporated. The so-obtained residue was diluted with 100 ml. of water, acidified with 10% cold hydrochloric acid and extracted with ether. The ether extract was worked up and gave 20β-tetrahydropyranyloxy-5-oxo-3,5-seco-A-nor-pregnan-3-oic acid as a colorless viscous oil.

EXAMPLE 118

A solution of 5,17-dioxo-3,5-seco-A-nor-androstan-3-oic acid in methanol was neutralized with 1N lithium methylate solution against phenolphthaleine. The solution was evaporated to dryness, the residue dissolved in benzene and the so-obtained solution evaporated yielding 5,17-dioxo-3,5-seco-A-nor-androstan-3-oic acid lithium salt as an amorphous powder.

5 g. of the above lithium salt was refluxed in 100 ml. of quinoline for 6 hours. After cooling, the reaction mixture was filtered and the filtrate was poured on a mixture of 150 g. of ice and 100 ml. of conc. hydrochloric acid and extracted with ether. The ether extract was worked up and chromatographed on aluminium oxide. The fractions obtained with hexane-benzene (5:1) were evaporated and gave, on addition of hexane, 10α-desA-androstane-5,17-dione, m.p. 121.5°–122° (crystallized from ethyl acetatehexane).

EXAMPLE 119

5.56 g. of 17β-hydroxy-5-oxo-3,5-seco-A-nor-androstan-3-oic acid lithium salt (prepared by treating the free acid with 1N lithium methylate according to the procedure of Example 116) was refluxed in 100 ml. of quinoline at a bath temperature of 260° for 2 hours. The reaction mixture was then poured on ice and taken up in ether. The ether extract yielded on working up an amorphous residue, which was oxidized with 15 ml. of Jones reagent in 150 ml. of acetone at 0°. The reaction mixture was then worked up and the crude product obtained was refluxed with 60 ml. of 2N sodium methylate solution for 1 hour. Chromatography of the reaction product followed by recrystallization from ether-petroleum ether yielded pure 10β-desA-androstane-5,17-dione.

The same compound was obtained in an analogous manner starting with 17β-hydroxy-5-oxo-3,5-seco-A-nor-androstan-3-oic acid sodium salt.

EXAMPLE 120

4.85 g. of 17β-benzolyoxy-5-oxo-3,5-seco-A-nor-androstan-3-oic acid lithium salt (prepared by treating the free acid with 1N lithium methylate according to the procedure of Example 116) was refluxed in 100 ml. of quinoline for 7 hours. The reaction mixture was then extracted with ether. The extract was washed with hydrochloric acid, sodium hydroxide solution and water and the crude product was then re-benzoylated with benzoyl chloride in pyridine. Chromatography on silica gel gave 17β-benzoyloxy-10α-desA-androstan-5-one, m.p. 110°–111° (crystallized from acetonehexane), $[\alpha]_D^{25} = 48°$ (dioxane).

The same product was obtained by pyrolyzing the lithium salt in a mixture of 15 g. of sodium acetate and potassium acetate at 0.5–0.05 mm. Hg and 275°–320° for 2 hours and analogous working up of the distillate.

The same or better yields were achieved by carrying out the pyrolysis in sodium phenylpropionate, sodium phthalate or sodium propionate. Furthermore, sodium salicylate, sodium benzoate, sodium terephthalate and sodium furoate were also used as the reaction medium.

EXAMPLE 121

1.5 g. of 17α-methyl-17β-hydroxy-desA-9β,10β-androstan-5-one was dissolved in 30 ml. of acetic anhydride and after the addition of 200 mg. of anhydrous sodium acetate refluxed for 2 hours. The reaction mixture was evaporated, the residue was taken up in ether and the extract was worked up yielding 17α-methyl- 17β-acetoxy-desA-9β,10β-androstan-5-one, m.p. 124°–125°, [α]$_D^{25}$ = −16° (dioxane).

EXAMPLE 122

A solution of 1 g. of testosterone in 10 ml. of pyridine was refluxed under nitrogen with a solution of 1 ml. of monochlorodimethyl ether in 20 ml. of pyridine at 115°–120° for 2 hours. The reaction mixture was then poured on ice and extracted with ether. The ether extract was worked up yielding testosterone-17β-methoxymethyl ether, m.p. 120°–122°.

This compound was treated with sodium metaperiodate and potassium permanganate according to the procedure of Example 114 and the resulting seco acid was pyrolyzed according to the procedure of Example 110. There are thus obtained 17β-methoxymethyloxy-desA-androstan-5-one, an oil, as a mixture of the 10α- and the 10β-isomer.

EXAMPLE 123

To 15.0 g. of 5% rhodium/alumina catalyst in a 3 liter round bottom flask was added 120 ml. of 3N hydrochloric acid followed by 300 ml. of absolute ethanol. The so-obtained mixture was prereduced by being shaken for 25 minutes under hydrogen.

To the so-prepared prereduced mixture was added a solution of 30.0 g. of 17β-hydroxy-desA-androst-9-en-5-one in 900 ml. of absolute ethanol. The reaction mixture was then hydrogenated for 60 minutes, at which point the rate of uptake leveled off and the reaction was stopped. The catalyst was removed by filtration over a filter aid (Celite), the filtrate was neutralized with saturated aqueous sodium bicarbonate, and the solution was concentrated in vacuo to ca. 350 ml. This concentrate was then extracted with ether (3 × 350 ml.), the organic phase was washed with water (3 × 225 ml.) and saturated sodium chloride (2 × 225 ml.), and dried over anhydrous sodium sulfate.

The ether solution was filtered and concentrated on the steam bath to a final solution of 80–100 ml., cooled at room temperature for 3 hours, then overnight at −20°, yielding as white crystals, 17β-hydroxy-9β,10β-desA-androstan-5-one which was dissolved in the minimum amount of anhydrous ether and the ether solution was concentrated down to about one-tenth original volume and the solution then was cooled one hour at room temperature, then overnight at 20°. The crystals were then separated and melted at 143°–145.5°, [α]$_D^{25}$ = −12.9° (CHCl$_3$, C = 1.065%).

EXAMPLE 124

A solution of 10.0 g. of 11α-mesoxy-5,20-dioxo-3,5-seco-A-nor-pregnane-3-oic acid in 100 ml. glacial acetic acid was refluxed under a nitrogen atmosphere for 40 minutes. The solution was then concentrated at 50°–55° (water pump), the brown residue was taken up in ether, washed with water and dried over sodium sulfate. Evaporation of the solvent afforded Δ$^{9(11)}$-5,20-dioxo-3,5-seco-A-nor-pregnene-3-oic acid.

The sodium salt of Δ$^{9(11)}$-5,20-dioxo-3,5-seco-A-nor-pregnene-3-oic acid was prepared by treating a solution of 7.5 g. of the acid, in 50 ml. of methanol, with a slight excess of sodium methoxide (1.3 g.). The final solution (pH 8–9; indicator paper) was taken to dryness at the water pump, bath temperature 55° and stripped with benzene (2 × 10 ml.). The tan colored semi-solid residue was thoroughly blended with 25.0 g. of sodium phenylacetate and pyrolyzed for 3 hours, bath temperature 295°, internal temperature ca. 250°, initial pressure 100 microns (diffusion pump) and final pressure 30 microns. The total contents of the reaction vessel (hard, brown resin) were partitioned between water (300 ml.) and ether (100 ml.). The aqueous phase was extracted with ether (3 × 100 ml.); the ether phase was washed with water (2 × 100 ml.) and dried over sodium sulfate, yielding a yellow oil which was triturated with ether and cooled at 0°, affording desA-pregnan-9-ene-5,20-dione as slightly yellow crystals, which upon recrystallization from a small volume of ether melted at 112°–115° (sintering).

EXAMPLE 125

A mixture of 10 g. of 11α-mesoxy-5,20-dioxo-3,5-seco-A-norpregnane-3-oic acid and 100 g. of 1:1 (by weight) mixture of fused sodium acetate and fused potassium acetate was charged to a 250 ml. stirred flask which was equipped with a gas inlet tube and an air condenser protected with a salt bath. The reaction mixture was then heated at 275°–300° for 3 hours while a gentle stream of nitrogen was passed over the surface of the melt. With stirring the mixture was cooled to 90°, 100 ml. of water and 35 ml. of methylene chloride were added and stirring was continued until all of the salt had dissolved. The aqueous layer was then extracted with 2 × 100 ml. of methylene chloride and the combined organic extract, after being washed with 2 × 75 ml. of 2N sodium carbonate and 2 × 100 ml. of water was dried with sodium sulfate and evaporated. The neutral residual oil was determined by thin layer chromatographic analysis (silica gel, with ethyl acetate-benzene 2:1, developed by means of sulfuric acid-methanol, 1:1 V/V and 10% phosphomolybdic acid-methanol sprays) to contain by weight ca. 60% desA-pregn-9-ene-5,20-dione.

EXAMPLE 126

To a solution of 200 mg. of 11α-hydroxy-10α-desA-pregnane-5,20-dione in 1 ml. pyridine, 0.2 ml. of acetic anhydride was added, and the mixture was then allowed to stand overnight at room temperature. It was then poured into water and the resultant suspension extracted with chloroform. The extract was washed with water, dried over anhydrous sodium sulfate, and evaporated. The crystalline residue was recrystallized from ethyl acetate-petroleum ether giving 11α-hydroxy-10α-desA-pregnane-5,20-dione acetate, m.p., 157°–158°.

EXAMPLE 127

One mole of 11α-hydroxy-10β-desA-pregnane-5,20-dione was acetylated with one mole of acetic anhydride in pyridine. The crude product, obtainable in quantitative yield, was recrystallized from ether-petroleum ether to give 11α-hydroxy-10β-desA-pregnane-5,20-dione acetate, m.p. 127°–129°.

EXAMPLE 128

A solution of 6.4 g. of 11α-acetoxy-progesterone in 100 ml. ethyl acetate and 50 ml. methylene chloride was ozonized at −70° until the solution became blue in color. After oxygen was passed through, the solution was evaporated at room temperature in vacuo. The sirupy residue was dissolved in 100 ml. of glacial acetic acid, and after addition of 5 ml. of 30% hydrogen peroxide, kept at 2° for 24 hours. The reaction mixture was then evaporated to dryness, the residue dissolved in 1 liter of ether, and the ether solution extracted ten times, each time with 50 ml. portion of 2N sodium carbonate solution. The combined carbonate extracts were acidified with concentrated hydrochloric acid and the noncrystalline precipitate was extracted with methylene chloride. The combined extracts were dried over anhydrous sodium sulfate and evaporated to dryness in vacuo. The residue was chromatographed on a Florisil column and eluted with ethyl acetate. Upon evaporation of the solvent, the crystalline product obtained gave, after several recrystallizations from methylene chloride-hexane, 11α-hydroxy-5,20-dioxo-3,5-seco-A-nor-pregnan-3oic acid acetate, m.p. 171°–172°, $[\alpha]_D^{25} = 64.6°$, (c = 1, in chloroform).

EXAMPLE 129

A solution of 4.5 g. of 11α-hydroxy-5,20-dioxo-3,5-seco-A-nor-pregnan-3-oic acid acetate in one equivalent of aqueous sodium carbonate solution was evaporated to dryness in vacuo. The residual sodium salt was mixed well with 15 g. of sodium phenylacetate and the mixture pyrolyzed at 290° in vacuo (0.02 mm.) for 2.5 hours. The crude sublimate was chromatographed on a silica gel column and elution with petroleum ether/ether (3:7) gave a fraction which was recrystallized from acetone/petroleum ether. This gave 11α-hydroxy-10β-desA-pregnane-5,20-dione, which was identified by mixed melting point, and by comparison of optical rotation with a sample of the same compound prepared by the procedure of Example 7.

EXAMPLE 130

To a solution of 1.5 g. of 17β-hydroxy-17α-methyl-10α-desA-androstan-5-one in 100 ml. of carbon tetrachloride was added 1.62 g. of sulfuryl chloride dissolved in 75 ml. of carbon tetrachloride, and the reaction mixture stirred and heated at 45° for 24 hours. It was then transferred to a separatory funnel, washed with water, dried over sodium sulfate and evaporated. Separation by preparative thin layer chromatography gave 10β-chloro-17β-hydroxy-17α-methyl-desA-androstan-5-one, which was recrystallized from acetonehexane, m.p. 127°–128°, $[\alpha]_D^{25} = 59.2°$ (c = 0.5 in chloroform).

EXAMPLE 131

A mixture of 1.75 g. of crude chlorination product, obtained by the procedure of Example 130, and 4.3 g. of lithium carbonate in 100 ml. of dimethylformamide was stirred and heated at 100° for 3 hours. After cooling to room temperature, it was diluted with 1.5 liters of ether, and washed successively with water, 1N hydrochloric acid, and water, dried over sodium sulfate, and evaporated. Separation on preparative thin layer chromatograms gave crude non-crystalline 17β-hydroxy-17α-methyl-desA-androst-9-en-5-one.

EXAMPLE 132

A solution of 2 g. of 17β-hydroxy-10α-desA-androstan-5-one in 2 ml. of pyridine and 2 ml. of acetic anhydride was kept overnight at room temperature, and then poured into 50 g. of crushed ice. After two hours, the crystalline precipitate was collected by filtration, washed with water, and dried, giving 17β-acetoxy-10α-desA-androstan-5-one, m.p. 69.5°–70.5°, $[\alpha]_D^{25} = -6°$ (c = 0.5 in chloroform).

EXAMPLE 133

To a solution of 1 g. of 17β-acetoxy-10α-desA-androstan-5-one in 50 ml. of carbon tetrachloride was added dropwise a solution of 0.936 g. of sulfuryl chloride (2 mole equivalents) in 103 ml. of carbon tetrachloride. The reaction mixture was illuminated with a 250-watt infrared lamp during stirring at 40°–50° for 160 hours. It was then washed with water, 2N sodium carbonate solution, and with water again, dried over sodium sulfate and evaporated. A crystalline product was obtained which contained (gas-liquid chromatography) starting material and 17β-acetoxy-10β-chloro-desA-androstan-5-one.

To a solution of 1 g. of 17β-acetoxy-10α-desA-androstan-5-one in 150 ml. of carbon tetrachloride was added 75 mg. of benzoylperoxide and dropwise a solution of 0.936 g. of sulfuryl chloride in 100 ml. carbon tetrachloride. The reaction mixture was then stirred at room temperature for 160 hours. It was worked up in the same way as in Example 133 yielding a crystalline product which contained starting material and 17α-acetoxy-10β-chloro-desA-androstan-5-one.

To a solution of 0.5 g. of 17β-acetoxy-10α-desA-androstan-5-one in 50 ml. of acetic acid-carbon tetrachloride (1:9 v/v) was added in four portions 0.332 g. (1.33 mole equivalents) of sulfuryl chloride dissolved in 20 ml. acetic acid-carbon tetrachloride (1:9). The second, third and fourth portions were added 7, 24 and 96 hours respectively, after addition of the first. The reaction mixture was stirred at room temperature and worked up after 120 hours. A crystalline product containing starting material and 17β-acetoxy-10β-chloro-desA-adndrostan-5-one was obtained.

Recrystallization of the crude products obtained in the above experiments from ether gave 17β-acetoxy-10β-chloro-desA-androstan-5-one, m.p. 137°–141°, $[\alpha]_D^{25} = 93.8°$ (c = 0.5 in chloroform).

EXAMPLE 134

A mixture of 0.5 g. of 17β-acetoxy-10β-chloro-desA-androstan-5-one and 1.18 g. of lithium carbonate in 50 ml. of dimethylformamide was stirred at 100° for two and three-quarter hours. After cooling to room temperature, the mixture was diluted with 750 ml. of ether, and the ether solution washed with water, 1N hydrochloric acid, aqueous 2N sodium carbonate, and again with water, dried over sodium sulfate and evaporated giving 17β-acetoxy-desA-androst-9-en-5-one, m.p. 65°–70°, $[\alpha]_D^{25} = -25.2°$ (c = 1.05 in chloroform).

Alternatively, the crude products of the chlorinations of Example 133 were, without purification, dehydrochlorinated under the above conditions, and 17β-acetoxy-desA-androst-9-en-5-one isolated by preparative thin layer chromatography.

EXAMPLE 135

A solution of 1.5 g. of 11α-mesoxy-5,20-dioxo-3,5-seco-A-nor-pregnan-3-oic acid in 45 ml. of methanol was mixed with 0.385 g. of sodium carbonate in 15 ml. of water and evaporated to dryness. The last trace of water was removed by adding benzene and evaporating to dryness again. To the residual salt was added 50 ml. of freshly distilled triethanolamine, and the reaction mixture was then heated for 3–4 hours in a metal bath of 215°–220° under a nitrogen atmosphere. The temperature of the reaction solution varied between 190° and 205°. After cooling, the reaction mixture was diluted with 1 liter of water, and extracted with ether (10 × 150 ml.). The combined ether extracts were washed with water, 1N, hydrochloric acid, and with water again, dried and evaporated, yielding a crude product which was determined by ultraviolet spectroscopy and by gas chromatography to contain a substantial amount of desA-pregn-9-ene-5,20-dione. When the reaction time was extended to 5 to 6 hours, the yield dropped slightly.

A solution of 2.418 g. of the crude product obtained by the foregoing procedure and 1.4 g. of semicarbazide in 60 ml. of 95% ethanol and 9 ml. of glacial acetic acid was stirred and refluxed for 2 hours. After cooling in ice, the precipitate was filtered off and washed with ethanol. Evaporation of the mother liquors and crystallization from 10 ml. of 95% ethanol gave additional product. Both crops were combined, suspended in 100 ml. of 95% ethanol, refluxed for one hour, and concentrated to a volume of 50 ml., cooled in an ice bath, and filtered, giving desA-pregn-9-ene-5,20-dione disemicarbazone, which does not melt below 340°, but showed slight decomposition above 270°.

A solution of 1.87 g. of the so-formed disemicarbazone in 75 ml. acetic acid, 25 ml. of water, and 6.5 ml. of 1.66N pyruvic acid was warmed for two minutes at 40°, then left overnight at room temperature. It was then diluted with 1.5 liters of ether, washed with water, aqueous 2N sodium carbonate, and with water again, dried, and evaporated. The crystalline residue was dissolved almost completely in 50 ml. of hot heptane, filtered, and the filtrate was evaporated. The last operation was repeated with the residue and 20 ml. of heptane, and the so-obtained residue recrystallized from ether, yielding desA-pregn-9-ene-5,20-dione, which melted at 113°–113.5°, $[\alpha]_D^{25} = 54.1°$ (c = 1 in chloroform).

EXAMPLE 136

20$\beta$-Hydroxy-desA-pregn-9-en-5-one was reacted with semicarbazide in a (10:1 v/v) ethanol/acetic acid solution to give 20$\beta$-hydroxy-desA-pregn-9-en-5-one semicarbazone as colorless needles, m.p. 196°–198° ex ethyl acetate, $[\alpha]_D^{25} = 110°$ (c = 0.5 in ethanol).

EXAMPLE 137

A solution of 524 mg. of desA-pregn-9-ene-5,20-dione in absolute methanol (65 ml.) was stirred at 5°. Over a period of forty minutes, sodium borohydride (0.5 g.) was then added thereto. The total reaction time allowed was one hour. Cold glacial acetic acid was then added dropwise until the pH was about 7.5, the solution was concentrated to dryness in vacuo, chloroform (150 ml.) added, and the solution washed with water until it was neutral. The organic layer was then dried with sodium sulfate, and evaporated to dryness, yielding a clear oil. Chloroform (50 ml. dried over silica gel) was added to 552 mg. of this oil, and stirred with 10 g. of precipitated manganese dioxide (Code No. 37, General Metallic Oxides) for 19 hours. The suspension was then filtered through a sintered-glass funnel using a filter aid (Celite), and evaporated to dryness in vacuo giving a colorless oil. Crystallization of 520 mg. of this oil gave 20$\beta$-hydroxy-desA-pregn-9-en-5-one as colorless needles, m.p. 116°–122°. A further amount of this compound was isolated from thin layer chromatograms. At the same time, a second band which was fluorescent under ultraviolet light was eluted giving 20$\alpha$-hydroxy-desA-pregn-9-en-5-one, which was acetylated with acetic anhydride in pyridine giving 20$\alpha$-hydroxy-desA-pregn-9-en-5-one acetate, as colorless needles, m.p. 87°–89° ex ether/petroleum ether, $[\alpha]_D^{25} = -37.8°$ (c = 0.312 in ethanol).

EXAMPLE 138

20$\beta$-Hydroxy-desA-pregn-9-en-5-one (0.250 g.) was dissolved in 2 ml. of (1:1 v/v) acetic anhydride in pyridine and allowed to stand overnight. The solution was then poured onto crushed ice and the crystalline precipitate collected and sucked dry. The residue was crystallized from methanol/water giving 20$\beta$-acetoxy-desA-pregn-9-en-5-one as needles which were recrystallized from petroleum ether yielding the product as colorless needles, m.p. 84°–85°, $[\alpha]_D^{25} = 12.6°$ (c = 0.5 in ethanol).

EXAMPLE 139

A suspension of 238 mg. of 5% rhodium on alumina catalyst in a mixture of 26 ml. of 95% ethanol and 5.25 ml. of 2N aqueous sodium hydroxide was prereduced. To this was then added a solution of 262 mg. of 17$\beta$-hydroxy-desA-androst-9-en-5-one in 15 ml. 95% ethanol, and the whole mixture hydrogenated at room temperature and atmospheric pressure. After one mole equivalent of hydrogen was absorbed, the reaction was stopped, and the catalyst was separated by filtration. After standing overnight the filtrate was concentrated in vacuo. To the residue was added 1 ml. of glacial acetic acid, and the so-formed mixture dissolved in 1 liter of ether. The resultant clear solution was washed with 2N aqueous sodium carbonate solution, then with water, then dried over anhydrous sodium sulfate and evaporated to dryness in vacuo, yielding a pale yellow oil containing a substantial amount of 17$\beta$-hydroxy-9$\beta$,10$\beta$-desA-androstan-5-one.

EXAMPLE 140

20$\beta$-Hydroxy-9$\beta$,10$\beta$desA-pregnan-5-one (45 mg.) was dissolved in pyridine (0.1 ml). and acetic anhydride (0.1 ml.) and the reaction mixture allowed to stand overnight at room temperature, evaporated to dryness in vacuo, and passed through a silica gel column. The crystalline fraction was recrystallized from aqueous methanol giving 20$\beta$-acetoxy-9$\beta$,10$\beta$-desA-pregnan-5-one as colorless needles which upon crystallization from petroleum and then from ether/petroleum ether formed colorless needles, m.p. 100°–100.5°, $[\alpha]_D^{25} = 27.1°$ (c = 0.5 in ethanol).

EXAMPLE 141

Hydrogenation of 1 g. of 20$\beta$-hydroxy-desA-pregn-en-5-one was performed under acidic conditions according to the procedure of Example 15. After separation of catalyst an excess of 20 ml. 2N sodium hydroxide solution was added and allowed to stand overnight. The solution was acidified, dissolved in ether, and washed with sodium carbonate and water, dried and evaporated to dryness yielding a colorless oil which was dissolved in benzene (3 ml.) with warming. A solution (3 ml., equivalent to about 50% excess) of sodium t-amylate in benzene was added in the cold under a nitrogen atmosphere and the reaction mixture allowed to stand for one hour at room temperature. Freshly distilled (b.p. 80°) methyl vinyl ketone (2 ml. in 4 ml. of dry benzene) was then added thereto in six equal portions at a regular interval during the course of two hours. The resultant suspension was then refluxed for two hours, and allowed to stand overnight. The reaction mixture was acidified with glacial acetic acid, dissolved in ether, washed with 2N aqueous sodium carbonate and water, dried over sodium sulfate and evaporated to give a yellow oil. From this oil two fractions were separated by preparative thin layer chromatography [twenty-five (1 mm. thick) silicic acid plates]. First fraction was further purified by column chromatography giving 20$\beta$-hydroxy-9$\beta$,10$\beta$-desA-pregnan-5-one. The second fraction was further fractionated by preparative thin layer chromatography to give an oily product which was dissolved in methylene chloride (50 ml.), and oxidized with chromic acid in acetic acid solution (1 ml.), washed with bisulfite, and the organic layer dried and evaporated yielding an oily product which was purified by thin layer chromatography giving an oil, which crystallized upon addition of a drop of ethanol. Recrystallization from ethanol yielded 9β,10α-pregn-4-ene-3,20-dione as colorless needles, m.p. 163–164°.

EXAMPLE 142

The crude product of the hydrogenation of Example 141 was dissolved in benzene (3 ml.) with warming. A solution (3 ml., equivalent to about 50% excess) of sodium t-amylate in benzene was then added thereto in the cold under a nitrogen atmosphere and the reaction mixture allowed to stand for one hour at room temperature. 4-Diethylaminobutan-2-one (3 g. in 4 ml. dry benzene) was added in six equal portions at regular intervals during the course of two hours. The resultant suspension was then refluxed for two hours, and allowed to stand overnight. The reaction mixture was acidified with glacial acetic acid, dissolved in ether, washed with 2N aqueous sodium carbonate and water, dried over sodium sulfate, and evaporated to give a yellow oil. By using the same procedure as in Example 141 after chromic acid oxidation, crystalline material was isolated which was purified, giving 9β,10α-pregn-4-ene-3,20-dione, m.p. and mixed m.p. 163°–164°.

EXAMPLE 143

The crude product of the hydrogenation according to the procedure of Example 141 of 1.2 g. of 20β-hydroxy-desA-pregn-9-en-5-one was dissolved in benzene (5 ml.). A solution (3 ml., equivalent to about 50% excess) of sodium t-amylate in benzene was then added thereto in the cold under a nitrogen atmosphere, and the reaction mixture allowed to stand for one hour at room temperature. 4-Diethylaminobutan-2-one methiodide (6 g., m.p. 85°–86° ex acetone/chloroform) as a suspension in benzene (5 ml.) was added in six equal portions at regular intervals during the course of two hours. The resultant suspension was then refluxed overnight. The reaction mixture was acidified with glacial acetic acid, dissolved in ether, washed with 2N aqueous sodium carbonate and water, dried over sodium sulfate, and evaporated to give a yellow oil. By using the same procedure as in Example 141, after chromic acid oxidation, crystalline material was isolated, which afforded after recrystallization 9β,10α-pregn-4-ene-3,20-dione, m.p. and mixed m.p. 163°–164°.

EXAMPLE 144

To the solution of 108 mg. of 20β-hydroxy-9β,10β-desA-pregnan-5-one (regenerated from its acetate by hydrolysis using aqueous sodium hydroxide) in ethanol (8.2 ml.) was added 1 ml. of sodium ethoxide solution (prepared by dissolving 2.36 g. of sodium to make 250 ml. of an ethanolic solution) i.e. 1 mole of sodium ethoxide per mole of 20β-hydroxy-9β,10β-desA-pregnan-5-one. The reaction mixture was then allowed to stand for half an hour and freshly distilled 4-diethylaminobutan-2-one (0.5 ml.) added thereto, and the resultant mixture allowed to stand for two hours. Refluxed for one and one-half hours, and added two more portions (0.5 ml. each) of 4-diethylaminobutan-3-one in the cold under a nitrogen atmosphere. The solution was refluxed for one hour between the last two additions, and then overnight. The solution was cooled to room temperature and acidified using glacial acetic acid, poured into 10N sodium carbonate solution (100 ml.) on an ice-bath, extracted with ether (4 × 100 ml.) and methylene chloride (4 × 100 ml.), and washed with water. Evaporation then gave a pale yellow oil which was processed according to procedure of Example 141 and which after oxidation with chromic acid yielded 9β,10α-pregn-4-ene-3,20-dione, m.p. and mixed m.p. 163–164°.

EXAMPLE 145

To a solution of 0.104 g. of 20β-hydroxy-9β,10β-desA-pregnan-5-one (prepared via a crystalline acetate by saponification) in ethanol (2 ml.) was added 0.4 ml. "Triton B" (35% of benzyltrimethylammonium hydroxide in methanol). A solution of freshly distilled methyl vinyl ketone (0.08 g.) in ethanol (4 ml.) was then added to the reaction mixture under a nitrogen atmosphere. After refluxing for two hours, the reaction mixture was cooled and acidified with 3N hydrochloric acid (1 ml.) and again heated on a steam bath for ten minutes. The reaction mixture was then again cooled and poured into crushed ice (10 g.) and taken up in 1 liter of ether. The ether layer was washed successively with 1N hydrochloric acid (50 ml.), water (50 ml.), 1N sodium bicarbonate solution, and water (3 × 50 ml.). The ether solution was then dried over sodium sulfate and evaporated giving a yellow oil which by using preparative thin layer plates was separated into unchanged starting material and a yellow oil, which crystallized spontaneously. Recrystallization from ethanol gave 20β-hydroxy-9β,10α-pregn-4-en-3-one as colorless needles ex ethanol, m.p. and mixed m.p. 175°–176°. After oxidation with chromic acid, the latter gave 9β,10α-pregn-4-ene-3,20-dione, m.p. and mixed m.p. 163°–164° ex ethanol.

EXAMPLE 146

To a solution of 200 mg. of desA-pregnan-9-ene-5,20-dione in 15.0 ml. of absolute ethanol there was added 40.4 mg. of 5% rhodium on alumina catalyst. To this mixture there was then added 0.4 ml. of 3N hydrochloric acid. The reaction mixture was then hydrogenated in a round bottom flask with moderate shaking at atmospheric pressure and room temperature. The hydrogenation was terminated at the end of 60 minutes and the reaction mixture neutralized to pH 7 with sodium carbonate, filtered over a filter aid (Celite) and concentrated in vacuo at 40°. The residue was taken up in ether, partitioned between ether and water, and the ether layer washed with brine, dried over sodium sulfate, and evaporated in vacuo at 25° yielding an oil which was recrystallized from ether yielding crude reaction product containing desA-9β,10β-pregnane-5,20-dione.

Utilizing the same procedure as above desA-pregnan-9-ene-5,20-dione was also hydrogenated to desA-9β,10β-pregnane-5,20-dione utilizing the following:

| Catalyst | Weight Ratio Catalyst to Substrate | Medium | Hydrogenation Time, Minutes | M.Moles of Acid/Mg. of Catalyst |
|---|---|---|---|---|
| 5% rhodium/ alumina | 1:5 | 3N HCl/ ethanol | 60 | 3/100 |
| 5% rhodium/ | 1:20 | " | 80 | 12/100 |

| Catalyst | Weight Ratio Catalyst to Substrate | Medium | Hydrogenation Time, Minutes | M.Moles of Acid/Mg. of Catalyst |
| --- | --- | --- | --- | --- |
| 5% rhodium/ carbon powder alumina | 1:5 | " | 55 | 30/100 |
| 5% ruthenium/ carbon powder | 1:5 | ethanol | 270 | neutral (i.e. no acid) |

EXAMPLE 147

A mixture of 200 mg. of 20β-acetoxy-desA-pregnan-9-en-5-one, 25 mg. of 5% rhodium on alumina catalyst, 0.4 ml. of 3N hydrochloric acid and 15 ml. of absolute ethanol was hydrogenated at atmospheric pressure and room temperature with moderate shaking of the flask containing the reaction mixture. The hydrogenation was terminated at the end of 45 minutes, the catalyst removed by filtration and the filtrate neutralized to pH 7 with 5% aqueous sodium bicarbonate. The so-obtained neutral mixture was then concentrated in vacuo at 45°, and partitioned between 40 ml. of dichloromethane and 20 ml. of water. The organic layer was then separated, washed with water, dried over aqueous sodium sulfate and concentrated in vacuo at 40° yielding 20β-acetoxy-desA-9β,10β-pregnan-4-one.

EXAMPLE 148

1.0 g. of 17β-hydroxy-desA-9β,10β-androstan-5-one was dissolved in 50 ml. of anhydrous benzene. Then 20 ml. of solvent was boiled off and, after flushing the reaction flask with nitrogen, 25 mg. of potassium t-butylate was added thereto. Another 10 ml. of the solvent was then boiled off and in the course of one hour, with stirring and refluxing, a solution of 0.5 ml. of 4-diethylaminobutan-2-one in 10 ml. of benzene was gradually added to the reaction mixture. The reaction mixture was then stirred and refluxed for a further hour, after which the reaction mixture was cooled and filtered through 10 g. of alumina (neutral, Grade III). The column was washed with 100 ml. of ether and the combined filtrates were evaporated, yielding a yellow reaction product which was dissolved in 30 ml. of benzene and chromatographed on a column of 100 g. of alumina (neutral, Grade III). Elution with benzene and benzene:ether (19:1) (10 fractions, 100 ml. each) yielded some unreacted starting material. The desired product, 9β,10α-testosterone, was then eluted with benzene:ether [(9:1), (4:1), and (2:1)] (6 fractions, 100 ml. each). Evaporation of these fractions and crystallization of the residue from diisopropyl ether yielded 9β,10α-testosterone, m.p. 153°–154°.

EXAMPLE 149

To a mixture of 100 g. of 17β-hydroxy-desA-9β,10β-androstan-5-one and 20 mg. of potassium hydroxide in 30 ml. of t-butanol at 60°, a solution of 0.455 g. of 4-diethylaminobutan-2-one in 5 ml. of benzene was added gradually in the course of 30 minutes under a nitrogen atmosphere with stirring. The reaction mixture was then stirred at 60° for an additional 30 minutes and then cooled to 20°. To the so-cooled reaction mixture, 0.1 ml. of acetic acid was added and the resulting mixture evaporated in vacuo at 30°. The crude product was then chromatographed as described in Example 148 and the fractions containing 9β,10α-testosterone (by thin layer chromatography) were combined, evaporated and the residue crystallized from ether yielding 9β,10α-testosterone, m.p. 155°–156°.

The same procedure as above was repeated utilizing isopropanol in place of t-butanol and effecting the reaction at 50° rather than 60°. The reaction so-conducted also yielded 9β,10α-testosterone.

EXAMPLE 150

To a mixture of 1.0 g. of 17β-hydroxy-desA-9β,10β-androstan-5-one and 20 mg. of potassium hydroxide in 30 ml. of t-butanol at 50°, a solution of 0.243 g. of 4-dimethylaminobutan-2-one was added gradually in the course of 30 minutes under a nitrogen atmosphere and with stirring. The reaction mixture was then stirred at 50° for an additional 30 minutes and then cooled to 20°. To the so-cooled reaction mixture 0.1 ml. of acetic acid was added and the resulting mixture evaporated in vacuo at 30°. The crude product was chromatographed as described in Example 148 and the fractions containing 9β,10α-testosterone (by thin layer chromatography) were combined, evaporated, and the residue crystallized from ether yielding 9β,10α-testosterone.

The same procedure as above was repeated but in place of the 4-dimethylaminobutan-2-one, 0.30 g. of 4-(N-pyrrolidyl)-butan-2-one was utilized. This reaction so-conducted also yielded 9β,10α-testosterone.

EXAMPLE 151

To a stirred solution of 1.0 g. of desA-9β,10β-androst-5,17-dione and 20 mg. of sodium hydroxide in 30 ml. of t-butanol maintained at 50° and under a nitrogen atmosphere, there was added gradually within the course of 30 minutes a solution of 0.30 g. of methyl vinyl ketone in 5 ml. of benzene. The reaction mixture was then stirred under a nitrogen atmosphere at 50° for an additional 30 minutes and then cooled to 20°. To the so-cooled reaction mixture 0.1 ml. of acetic acid was added and the resulting mixture evaporated in vacuo at 30°. The crude product was then chromatographed as described in Example 148 and the fractions containing 9β,10α-androst-4-ene-3,17-dione (by thin layer chromatography) were combined, evaporated, and the residue crystallized from ether yielding the product as crystals melting at 153°–154°.

EXAMPLE 152

A 57% sodium hydride in mineral oil dispersion (285 mg.) was washed free of oil with ether, and then suspended in 20 ml. dry dimethylformamide under a nitrogen atmosphere. 17β-(Tetrahydro-2-pyranyloxy)-9β,10β-desA-androstane-5-one (2.17 g.) in 20 ml. dry dimethylformamide was added in one portion to the sodium hydride suspension, and the reaction mixture was then stirred at 100° under a nitrogen atmosphere for 1 hour. The resulting solution was cooled to 20°, and 791 mg. of 1-chloro-3-butanone in 1 ml. dry dimethylformamide in one portion, was added thereto with stirring. After standing at 20° for 16 hours under a nitrogen atmosphere, the solution was evaporated in vacuo. The last traces of dimethylformamide were removed in high vacuo at about 80° bath temperature. The residual oil was dissolved in ethyl acetate, the ethyl acetate solution was washed with water, dried with sodium sulfate, and evaporated in vacuo giving an oil; 2.32 g. of which was dissolved in 24 ml. of 0.5N sodium methoxide in methanol. The mixture was then allowed to stand at 20° for 72 hours under a nitrogen atmosphere. It was then poured on ice and the pH was adjusted to 7.5 with 1N HCl. Most of the methanol was then evaporated off in vacuo and the residue was extracted at 20° with ethyl acetate. The ethyl acetate extract was washed with water, dried with sodium sulfate, charcoaled (with Norite A) and evaporated in vacuo giving an oil. This oil was placed in a mixture of 18 ml. of methanol and 6 ml. of 2N HCl and the resultant mixture was refluxed under a nitrogen atmosphere for 90 minutes. It was then poured on ice, neutralized with 1N NaOH, and concentrated in vacuo. The residue was extracted at 20° with ethyl acetate and ether. The combined extracts were then washed with aqueous sodium chloride, dried with sodium sulfate, charcoaled (with Norite A), and evaporated in vacuo giving an oil, which according to thin layer chromatography consisted of two main components, 17β-hydroxy-9β,10β-desA-androstane-5-one and 9β,10α-testosterone.

The above-described crude oil was chromatographed using a Florisil column (34 g. of adsorbent) with benzene, benzenechloroform and benzene-ethyl acetate eluents. First 17β-hydroxy-9β,10β-desA-androstane-5-one was eluted, followed by crude 9β,10α-testosterone. Mixed melting point determination with an authentic sample of 9β,10α-testosterone showed no depression of the melting point. Recrystallization from ether gave purified 9β,10α-testosterone, m.p. 155°–156°,[α]$_D^{25}$ = −150° (chloroform).

EXAMPLE 153

A 57% sodium hydride in mineral oil dispersion (84 mg., 2 m.moles) was washed free of oil with ether and then suspended in 8 ml. of dry dimethylformamide under a nitrogen atmosphere. 17β-Hydroxy-9β,10β-desA-androstane-5-one (236 mg., 1 m.mole) in 8 ml. of dry dimethylformamide was added to the stirred suspension, and the reaction mixture was heated under a nitrogen atmosphere at 55° for 1 hour. It was then cooled to 20°, and 117 mg. of 1-chloro-3-butanone was added in one portion. The reaction mixture was then stirred at 20° under a nitrogen atmosphere for 1 hour, poured on ice and neutralized with 1N HCl. The water and some dimethylformamide were evaporated in vacuo. The last of the dimethylformamide was removed in high vacuo at about 80° bath temperature. The residual oil was then dissolved in ethyl acetate, the ethyl acetate solution was washed with water, dried with sodium sulfate, and evaporated in vacuo giving crude product which was put in a mixture of 6 ml. methanol and 2 ml. of 2N HCl. The resultant mixture was refluxed under nitrogen for 90 minutes. It was then poured on ice, neutralized with 1N NaOH, and concentrated in vacuo. The residue was extracted with ethyl acetate and with ether. The combined extracts were washed with aqueous sodium chloride, dried with sodium sulfate, and evaporated in vacuo giving an oil containing as the two main components, 17β-hydroxy-9β,10β-desA-androstane-5-one and 9β,10α-testosterone. The latter compound can be separated by chromatographic means.

EXAMPLE 154

20β-Hydroxy-9β,10β-desA-pregnan-5-one (100 mg.) and 0.15 ml. of freshly distilled 1,3-dichloro-2-butene (b.p. 130°) in 0.3 ml. of dry benzene was cooled in an ice-bath. To the reaction mixture there was then added, in an atmosphere of dry nitrogen, sodium t-amylate solution (0.3 ml.) prepared by refluxing in an atmosphere of nitrogen 4.41 g. of t-amyl alcohol and 25 ml. of dry benzene over 1.77 g. sodium. The reaction mixture was then diluted with 7 ml. of benzene, washed with 2 ml. of water, dried with sodium sulfate, and concentrated to a volume of 2 ml. Chromatography of the so-concentrated solution on 50 g. of silicic acid using 1% ethyl acetate in benzene as the eluent gave a 50:50 (indicated by thin layer chromatography) mixture containing 3-chloro-20β-hydroxy-3-methyl-3,5-seco-9β,10α-A-nor-pregn-2-en-5-ones and the corresponding 10β-isomer.

The so-obtained substance was dissolved in methylene chloride, oxidized overnight with chromic acid solution (prepared from 40 mg. chromium trioxide dissolved in 0.2 ml. of water and 2 ml. of acetic acid), the resulting product containing 3-chloro-3-methyl-3,5-seco-9β,10α-A-nor-pregn-2-ene-5,20-dione was dissolved in an equal volume of cold concentrated sulfuric acid, diluted with water, extracted with methylene chloride, and refluxed in benzene in the presence of p-toluene sulfonic acid for one hour. The reaction mixture was washed with aqueous sodium carbonate solution, water, dried over sodium sulfate and evaporated to dryness yielding an oil. Thin layer chromatography yielded 9β,10α-progesterone.

EXAMPLE 155

A solution of 17β-hydroxy-9β,10β-desA-androstane-5-one in anhydrous benzene was reacted with dihydropyran in the presence of 1% p-toluene sulfonic acid in benzene according to the procedure of Example 109. This reaction yielded 17β-tetrahydropyranyloxy-9β,10β-desA-androstane-5-one, which upon recrystallization from ether/petroleum ether melted at 109°–111°,[α]$_D^{25}$ = +62.9 (in chloroform, c = 1%).

We claim:
1. A compound of the formula:

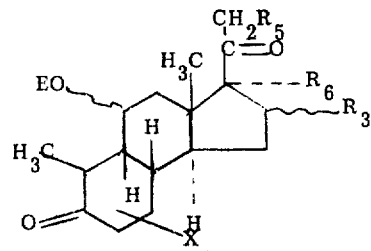

wherein R$_3$ is selected from the group consisting of hydrogen, fluoro, lower alkyl, hydroxy, benzoyloxy and lower alkanoyloxy; R$_6$ is selected from the group consisting of hydrogen, lower alkyl, hydroxy, benzoyloxy, lower alkanoyloxy and halogen; EO is benzoyloxy, lower alkanoyloxy or free hydroxy;

when $R_3$ and $R_6$ are hydroxy they may be taken together with an aldehyde or ketone to form an acetal or ketal of the formula:

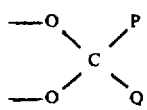

wherein P is individually selected from the group consisting of hydrogen and lower alkyl; Q is individually selected from the group consisting of lower alkyl, phenyl, phenyl substituted with radicals selected from the group consisting of halogen, lower alkoxy, hydroxy and lower alkyl, phenyl-lower-alkyl or phenyl-lower-alkyl aromatically substituted with radicals selected from the group consisting of halogen, lower alkoxy, hydroxy and lower alkylcyano; and P and Q taken together are lower alkylene; $R_5$ is selected from the group consisting of hydrogen and halogen; X is a substituent in the 6-position selected from the group consisting of hydrogen, lower alkyl, lower alkylthio and lower alkanoylthio or a substituent in the 7-position selected from the group consisting of hydrogen, lower alkyl, lower alkylthio, lower alkanoylthio and halogen.

2. A compound according to claim 1 wherein P and Q taken together are lower alkylene.

3. A compound of the formula:

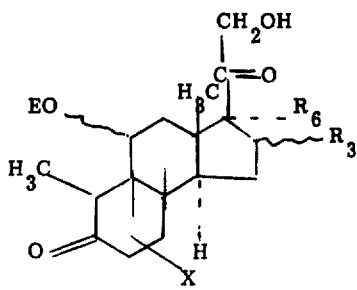

wherein $R_3$ is selected from the group consisting of hydrogen, fluoro, lower alkyl, hydroxy, benzoyloxy, and lower alkanoyl; $R_6$ is selected from the group consisting of hydrogen, lower alkyl, hydroxy, lower alkoxy, benzyloxy, benzhydryloxy, trityloxy, allyloxy, tetrahydropyranyloxy and halogen; EO is selected from the group consisting of benzoyloxy, lower alkanoyl, and hydroxy; and X is a substituent in the 6-position selected from the group consisting of hydrogen, lower alkyl, lower alkylthio and lower alkanoylthio or a substituent in the 7-position selected from the group consisting of hydrogen, lower alkyl, lower alkylthio, lower alkanoylthio and halogen.

4. A compound of the formula:

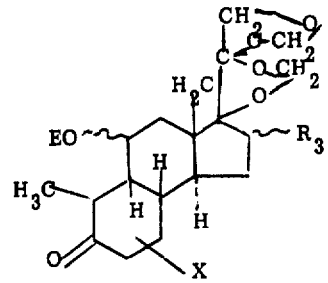

wherein $R_3$ is selected from the group consisting of hydrogen, fluoro, lower alkyl, hydroxy, benzoyloxy, and lower alkanoyl; EO is selected from the group consisting of benzoyloxy, lower alkanoyl, and hydroxy; and X is a substituent in the 6-position selected from the group consisting of hydrogen, lower alkyl, lower alkylthio and lower alkanoylthio or a substituent in the 7-position selected from the group consisting of hydrogen, lower alkyl, lower alkylthio, lower alkanoylthio, and halogen.

5. A compound of the formula:

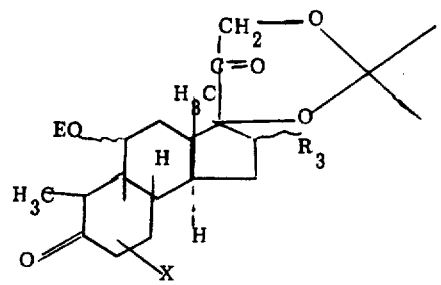

wherein $R_3$ is selected from the group consisting of hydrogen, fluoro, lower alkyl, hydroxy, benzoyloxy, and lower alkanoyl; EO is selected from the group consisting of benzoyloxy, lower alkanoyl and hydroxy; and X is a substituent in the 6-position selected from the group consisting of hydrogen, lower alkyl, lower alkylthio and lower alkanoylthio or a substituent in the 7-position selected from the group consisting of hydrogen, lower alkyl, lower alkylthio, lower alkanoylthio, and halogen.

* * * * *